US010596569B2

(12) United States Patent
Bohm et al.

(10) Patent No.: US 10,596,569 B2
(45) Date of Patent: Mar. 24, 2020

(54) SYSTEMS AND METHODS INCLUDING A ROTARY VALVE FOR AT LEAST ONE OF SAMPLE PREPARATION OR SAMPLE ANALYSIS

(71) Applicant: Ilumina, Inc., San Diego, CA (US)

(72) Inventors: Sebastian Bohm, San Diego, CA (US); Alex Aravanis, San Francisco, CA (US); Alexander Hsiao, Los Angeles, CA (US); Behnam Javanmardi, San Francisco, CA (US); Tarun Khurana, San Francisco, CA (US); Hai Quang Tran, San Diego, CA (US); Majid Aghababazadeh, San Francisco, CA (US); M. Shane Bowen, San Diego, CA (US); Boyan Boyanov, San Diego, CA (US); Dale Buermann, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/315,638

(22) PCT Filed: Jun. 3, 2015

(86) PCT No.: PCT/US2015/034053

§ 371 (c)(1),
(2) Date: Dec. 1, 2016

(87) PCT Pub. No.: WO2015/187868

PCT Pub. Date: Dec. 10, 2015

(65) Prior Publication Data

US 2017/0144155 A1 May 25, 2017

Related U.S. Application Data

(60) Provisional application No. 62/008,276, filed on Jun. 5, 2014.

(51) Int. Cl.
*G01N 35/08* (2006.01)
*B01L 3/00* (2006.01)
(Continued)

(52) U.S. Cl.
CPC ..... *B01L 3/502738* (2013.01); *B01L 3/50273* (2013.01); *B01L 3/502715* (2013.01);
(Continued)

(58) Field of Classification Search
CPC ......... B01L 2200/0673; B01L 2200/10; B01L 2300/069; B01L 2300/0851;
(Continued)

(56) References Cited

U.S. PATENT DOCUMENTS 6,958,132 B2 * 10/2005 Chiou .............. B01L 3/502792 204/600
2003/0162304 A1 8/2003 Dority et al.
(Continued)

FOREIGN PATENT DOCUMENTS

EP 1258720 A2 11/2002
EP 2143491 A1 1/2010
(Continued)

OTHER PUBLICATIONS

Bonomelli, Luca, Authorized Officer, European Patent Office, International Search Report and Written Opinion, International Patent Application No. PCT/US2015/034053, dated Nov. 30, 2015, 22 pages.

*Primary Examiner* — Dean Kwak
(74) *Attorney, Agent, or Firm* — Illumina, Inc.

(57) ABSTRACT

Systems and methods for conducting designated reactions that include a fluidic network having a sample channel, a reaction chamber, and a reservoir. The sample channel is in flow communication with a sample port. The system also includes a rotary valve that has a flow channel and is
(Continued)

configured to rotate between first and second valve positions. The flow channel fluidically couples the reaction chamber and the sample channel when the rotary valve is in the first valve position and fluidically couples the reservoir and the reaction chamber when the rotary valve is in the second valve position. A pump assembly induces a flow of a biological sample toward the reaction chamber when the rotary valve is in the first valve position and induces a flow of a reaction component from the reservoir toward the reaction chamber when the rotary valve is in the second valve position.

11 Claims, 17 Drawing Sheets

(51) Int. Cl.

| | |
|---|---|
| ***B01L 7/00*** | (2006.01) |
| ***F16K 99/00*** | (2006.01) |
| ***C12Q 1/6869*** | (2018.01) |

(52) U.S. Cl.

CPC .............. *B01L 7/52* (2013.01); *C12Q 1/6869* (2013.01); *F16K 99/0013* (2013.01); *F16K 99/0015* (2013.01); *F16K 99/0028* (2013.01); *G01N 35/08* (2013.01); *B01L 2200/10* (2013.01); *B01L 2300/0816* (2013.01); *B01L 2300/0867* (2013.01); *B01L 2400/0487* (2013.01); *B01L 2400/0644* (2013.01); *B01L 2400/0655* (2013.01); *F16K 2099/0084* (2013.01)

(58) Field of Classification Search

CPC ..... B01L 2300/0867; B01L 2400/0487; B01L 2400/0644; B01L 3/502738; B01L 3/502792; B01L 7/52; B01L 2200/12; B01L 2300/0654; B01L 2300/0809; B01L 2300/0874; B01L 2300/0887; B01L 2300/123; B01L 2300/1827; B01L 2400/0655; B01L 3/5027; B01L 3/502707; B01L 3/50273; B01L 3/527; G01N 2021/0307; G01N 2021/0325; G01N 2021/6417; G01N 2021/6441; G01N 21/6428; G01N 21/6486

USPC ................................ 422/502–505, 400, 417

See application file for complete search history.

(56) References Cited

U.S. PATENT DOCUMENTS

| | | | | |
|---|---|---|---|---|
| 2007/0062583 | A1* | 3/2007 | Cox | B01L 3/502715 137/565.01 |
| 2008/0153078 | A1* | 6/2008 | Braman | B01L 3/502 435/2 |
| 2008/0254467 | A1* | 10/2008 | Regan | B01L 3/5023 435/6.16 |
| 2010/0029915 | A1* | 2/2010 | Duthie | C12M 23/16 530/412 |
| 2011/0104024 | A1* | 5/2011 | Gransee | B01L 3/502738 422/502 |
| 2011/0201099 | A1* | 8/2011 | Anderson | G01N 21/05 435/287.2 |
| 2012/0178091 | A1 | 7/2012 | Glezer et al. | |
| 2012/0315635 | A1* | 12/2012 | Vangbo | G01N 27/44791 435/6.11 |
| 2013/0217106 | A1* | 8/2013 | Jones | B01L 3/5027 435/287.2 |
| 2013/0260372 | A1 | 10/2013 | Buermann et al. | |
| 2016/0356715 | A1* | 12/2016 | Zhong | G01N 21/645 |
| 2017/0016060 | A1* | 1/2017 | Sabounchi | B01L 3/5027 |

FOREIGN PATENT DOCUMENTS

| | | |
|---|---|---|
| JP | 2005518532 | 6/2005 |
| JP | 2009002899 | 1/2009 |
| JP | 2014507937 | 4/2014 |
| JP | 2006078276 | 3/2016 |
| RU | 2509533 | 3/2014 |
| WO | 2007130951 A2 | 11/2007 |
| WO | 2009/118444 | 10/2009 |
| WO | 2012042226 A2 | 4/2012 |
| WO | 2014/008381 | 1/2014 |
| WO | 2014008381 A2 | 1/2014 |

* cited by examiner

SYSTEMS AND METHODS INCLUDING A ROTARY VALVE FOR AT LEAST ONE OF SAMPLE PREPARATION OR SAMPLE ANALYSIS

CROSS-REFERENCE TO RELATED APPLICATIONS

This application is a national stage of PCT Application No. PCT/US2015/034053, entitled "SYSTEMS AND METHODS INCLUDING A ROTARY VALVE FOR AT LEAST ONE OF SAMPLE PREPARATION OR SAMPLE ANALYSIS", filed on Jun. 3, 2015, which claims priority from and the benefit of U.S. Provisional Application Ser. No. 62/008,276 filed on Jun. 5, 2014. Each of the foregoing applications is hereby incorporated by reference in its entirety.

BACKGROUND

Embodiments of the present application relate generally to systems and methods for generating samples for biochemical analysis and/or conducting biochemical reactions and, more particularly, to systems and methods utilizing a rotary valve.

Various biochemical protocols involve performing a large number of controlled reactions on support surfaces or within designated reaction chambers. The controlled reactions may be conducted to analyze a biological sample or to prepare the biological sample for subsequent analysis. The analysis may identify or reveal properties of chemicals involved in the reactions. For example, in an array-based, cyclic sequencing assay (e.g., sequencing-by-synthesis (SBS)), a dense array of DNA features (e.g., template nucleic acids) are sequenced through iterative cycles of enzymatic manipulation. After each cycle, an image may be captured and subsequently analyzed with other images to determine a sequence of the DNA features. In another biochemical assay, an unknown analyte having an identifiable label (e.g., fluorescent label) may be exposed to an array of known probes that have predetermined addresses within the array. Observing chemical reactions that occur between the probes and the unknown analyte may help identify or reveal properties of the analyte.

There has been a general demand for systems that automatically perform assays, such as those described above, in which the system requires less work by, or involvement with, the user. Presently, most platforms require a user to separately prepare the biological sample prior to loading the biological sample into a system for analysis. It may be desirable for a user to load one or more biological samples into the system, select an assay for execution by the system, and have results from the analysis within a predetermined period of time, such as a day or less. At least some systems used today are not capable of executing certain protocols, such as whole genome sequencing, that provide data having a sufficient level of quality and within a certain cost range.

BRIEF DESCRIPTION

In accordance with an embodiment, a system is provided that includes a fluidic network having a sample channel, a reaction chamber, and a reservoir. The sample channel is in flow communication with a sample port that is configured to receive a biological sample. The system also includes a pump assembly that is configured to be in flow communication with the fluidic network. The system also includes a rotary valve that has a flow channel and is configured to rotate between first and second valve positions. The flow channel fluidically couples the reaction chamber and the sample channel when the rotary valve is in the first valve position and fluidically couples the reservoir and the reaction chamber when the rotary valve is in the second valve position. The pump assembly induces a flow of the biological sample toward the reaction chamber when the rotary valve is in the first valve position and induces a flow of a reaction component from the reservoir toward the reaction chamber when the rotary valve is in the second valve position.

In an embodiment, a method is provided that includes rotating a rotary valve having a flow channel to a first valve position. The flow channel is in flow communication with a reaction chamber when in the first valve position. The method may also include flowing a biological sample from a sample channel or a first reservoir through the flow channel and into the reaction chamber when the rotary valve is in the first valve position. The method may also include rotating the rotary valve to a second valve position. The flow channel may fluidically couple a second reservoir and the reaction chamber when in the second valve position. The method may also include flowing a reaction component from the second reservoir into the reaction chamber. The reaction component interacts with the biological sample within the reaction chamber.

In an embodiment, a system is provided that includes a flow-control system having a fluidic network and a pump assembly that is in flow communication with the fluidic network. The fluidic network includes a sample channel that is configured to receive a biological sample, a plurality of reservoirs, and a reaction chamber. The system also includes a rotary valve having a flow channel. The rotary valve is configured to rotate to different valve positions to fluidically couple the reaction chamber to the sample channel or to one of the reservoirs. The system also includes a detection device that is configured to detect light signals from the reaction chamber during an assay protocol. The system also includes a system controller that is configured to control the rotary valve and the pump assembly to flow the biological sample from the sample channel and into the reaction chamber. The system controller is also configured to control the rotary valve, the pump assembly, and the detection device during a plurality of protocol cycles, wherein each of the protocol cycles includes: (a) rotating the rotary valve to a first reservoir-valve position such that the reaction chamber is in flow communication with a first reservoir of the plurality of reservoirs; (b) controlling the pump assembly to induce a flow of a fluid from the first reservoir into the reaction chamber; (c) rotating the rotary valve to a second reservoir-valve position such that the reaction chamber is in flow communication with a second reservoir of the plurality of reservoirs; (d) controlling the pump assembly to induce a flow of a fluid from the second reservoir into the reaction chamber; and (e) controlling the detection device to detect the light signals from the reaction chamber while the fluid from the second reservoir flows through the reaction chamber or after the fluid from the second reservoir flows through the reaction chamber.

In accordance with an embodiment, a method is provided that includes providing a microfluidic body and a rotary valve. The microfluidic body has a body side and a fluidic network that includes a supply port and a feed port. The supply port opens to the body side. The rotary valve is rotatably mounted to the body side. The rotary valve has a first channel port, a second channel port, and a flow channel that extends between the first channel port and the second channel port. The method also includes rotating the rotary valve to a first valve position at which the first channel port is in flow communication with the supply port of the microfluidic body. The method also includes flowing a biological sample through the first channel port and into the flow channel when the rotary valve is in the first valve position. The method also includes rotating the rotary valve to a second valve position with the biological sample within the flow channel such that the first channel port is sealed by the body side. The method also includes performing a thermocycling operation to change a temperature of the biological sample in the flow channel to a select temperature.

In accordance with an embodiment, a system is provided that includes a microfluidic body having a body side and a fluidic network that includes a supply port and a feed port. The supply port opens to the body side. The system also includes a rotary valve that is rotatably mounted to the body side. The rotary valve has a first channel port, a second channel port, and a flow channel that extends between the first and second channel ports. The rotary valve is configured to rotate between first and second valve positions. The first channel port is in flow communication with the supply port of the microfluidic body when the rotary valve is in the first valve position. The first channel port is sealed by the microfluidic body when the rotary valve is in the second valve position. The system also includes a pump assembly that is configured to induce a flow of a fluid through the supply port and into the flow channel when the rotary valve is in the first valve position. The system also includes a thermocycler that is positioned relative to the rotary valve and configured to control a temperature experienced by the fluid within the flow channel when the rotary valve is in the second valve position.

In accordance with an embodiment, a system is provided that includes a microfluidic body having a fluidic network that has an inlet port, an outlet port, and a sample reservoir. The system also includes a rotary valve that is rotatably coupled to the microfluidic body. The rotary valve has a first channel segment and a second channel segment. The first channel segment fluidically couples the inlet port and the sample reservoir when the rotary valve is in a first valve position. The second channel segment fluidically couples the outlet port and the sample reservoir when the rotary valve is in the first valve position. The system also includes a pump assembly configured to flow a fluid through the inlet port and the first channel segment into the sample reservoir when the rotary valve is in the first valve position. The rotary valve is configured to move to a second valve position in which the sample reservoir is sealed by the rotary valve. The system may also include a thermocycler that is positioned relative to the microfluidic body to provide thermal energy to the sample reservoir when the rotary valve is in the second valve position.

In accordance with an embodiment, a system is provided that includes a microfluidic body having a fluidic network that has a sample reservoir and a separate assay channel. The assay channel extends between first and second ports. The fluidic network also includes a feed port. The system may also include a thermocycler that is positioned adjacent to a thermal-control area of the microfluidic body. The assay channel extends through the thermal-control area. The thermocycler is configured to provide thermal energy to the thermal-control area. The system also includes a rotary valve that is rotatably coupled to the microfluidic body and configured to move between first and second valve positions. The rotary valve has a bridge channel and a separate flow channel. The bridge channel fluidically couples the sample reservoir and the first port of the assay channel and the flow channel fluidically couples the second port of the assay channel and the feed port when the rotary valve is in the first valve position. The rotary valve is configured to move to a second valve position to seal the first and second ports of the assay channel.

DETAILED DESCRIPTION

Figure 1:
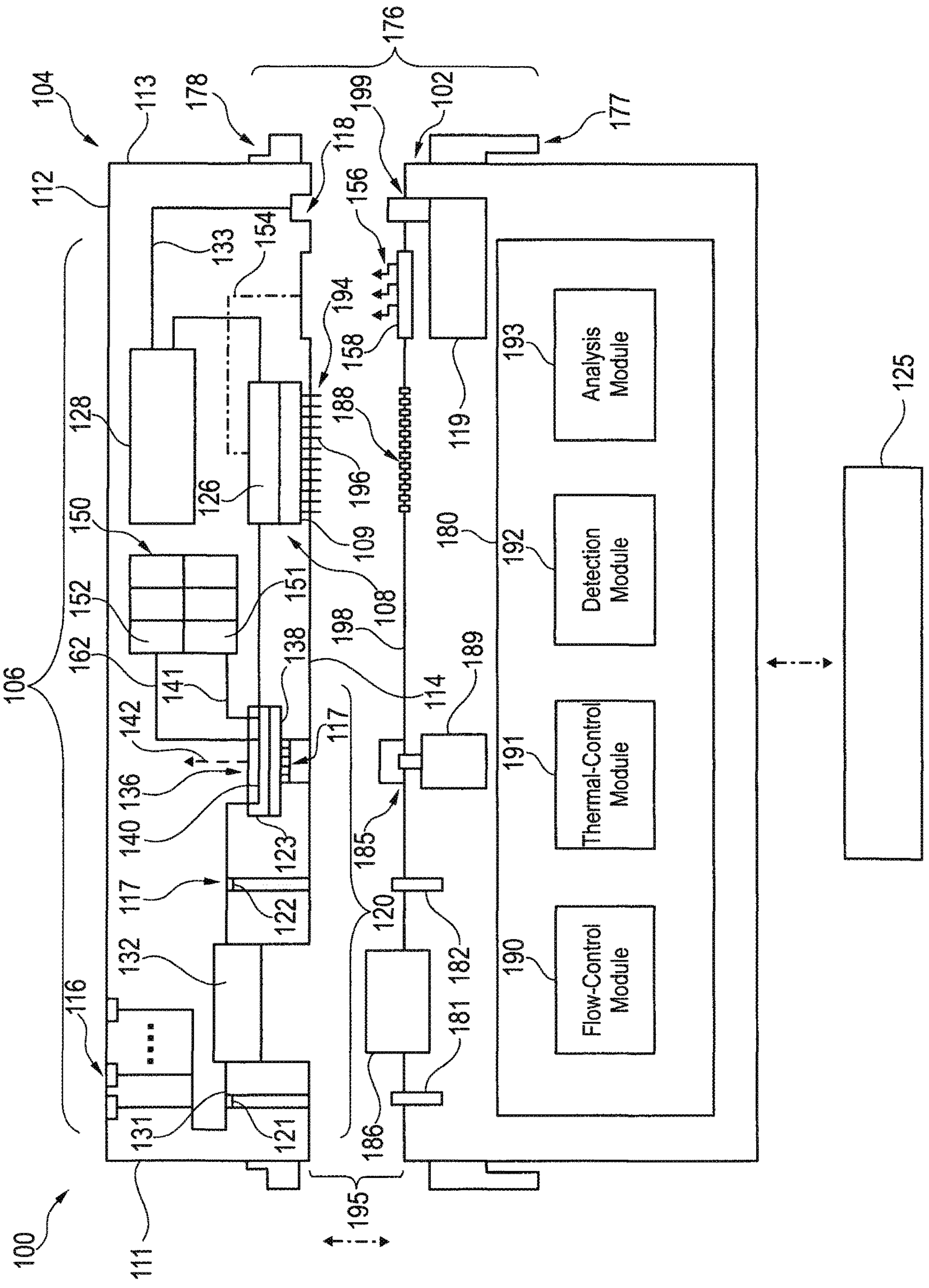
FIG. 1 is a schematic diagram of a system formed in accordance with an embodiment that is configured to conduct at least one of biochemical analysis or sample preparation.

Embodiments set forth herein may be used to perform designated reactions for sample preparation and/or biochemical analysis. As used herein, the term "biochemical analysis" may include at least one of biological analysis or chemical analysis. FIG. 1 is a schematic diagram of a system 100 that is configured to conduct biochemical analysis and/or sample preparation. The system 100 includes a base instrument 102 and a removable cartridge 104 that is configured to separably engage the base instrument 102. The base instrument 102 and the removable cartridge 104 may be configured to interact with each other to transport a biological sample to different locations within the system 100, to conduct designated reactions that include the biological sample in order to prepare the biological sample for subsequent analysis, and, optionally, to detect one or more events with the biological sample. The events may be indicative of a designated reaction with the biological sample. The removable cartridge 104 may be similar to an integrated microfluidic cartridge, such as those shown and described in U.S. Provisional Patent Application No. 62/003,264, filed on May 27, 2014, which is incorporated herein by reference in its entirety. Embodiments set forth herein, however, are not limited to integrated devices, but may also be used in larger systems.

Although the following is with reference to the base instrument 102 and the removable cartridge 104 as shown in FIG. 1, it is understood that the base instrument 102 and the removable cartridge 104 illustrate only one exemplary embodiment of the system 100 and that other embodiments exist. For example, the base instrument 102 and the removable cartridge 104 include various components and features that, collectively, execute a number of operations for preparing the biological sample and/or analyzing the biological sample. In the illustrated embodiment, each of the base instrument 102 and the removable cartridge 104 are capable of performing certain functions. It is understood, however, that the base instrument 102 and the removable cartridge 104 may perform different functions and/or may share such functions. For example, in the illustrated embodiment, the removable cartridge 104 is configured to detect the designated reactions using a detection assembly (e.g., imaging device). In alternative embodiments, the base instrument 102 may include the detection assembly. As another example, in the illustrated embodiment, the base instrument 102 is a "dry" instrument that does not provide, receive, or exchange liquids with the removable cartridge 104. In alternative embodiments, the base instrument 102 may provide, for example, reagents or other liquids to the removable cartridge 104 that are subsequently consumed (e.g., used in designated reactions) by the removable cartridge 104.

As used herein, the biological sample may include one or more biological or chemical substances, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and/or biologically active chemical compound(s), such as analogs or mimetics of the aforementioned species. In some instances, the biological sample may include whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes.

In some embodiments, the biological sample may include an added material, such as water, deionized water, saline solutions, acidic solutions, basic solutions, detergent solutions and/or pH buffers. The added material may also include reagents that will be used during the designated assay protocol to conduct the biochemical reactions. For example, added liquids may include material to conduct multiple polymerase-chain-reaction (PCR) cycles with the biological sample.

It should be understood, however, that the biological sample that is analyzed may be in a different form or state than the biological sample loaded into the system 100. For example, the biological sample loaded into the system 100 may include whole blood or saliva that is subsequently treated (e.g., via separation or amplification procedures) to provide prepared nucleic acids. The prepared nucleic acids may then be analyzed (e.g., quantified by PCR or sequenced by SBS) by the system 100. Accordingly, when the term "biological sample" is used while describing a first operation, such as PCR, and used again while describing a subsequent second operation, such as sequencing, it is understood that the biological sample in the second operation may be modified with respect to the biological sample prior to or during the first operation. For example, a sequencing step (e.g. SBS) may be carried out on amplicon nucleic acids that were produced from template nucleic acids that were amplified in a prior amplification step (e.g. PCR). In this case the amplicons are copies of the templates and the amplicons are present in higher quantity compared to the quantity of the templates.

In some embodiments, the system 100 may automatically prepare a sample for biochemical analysis based on a substance provided by the user (e.g., whole blood or saliva). However, in other embodiments, the system 100 may analyze biological samples that are partially or preliminarily prepared for analysis by the user. For example, the user may provide a solution including nucleic acids that were already isolated and/or amplified from whole blood.

As used herein, a "designated reaction" includes a change in at least one of a chemical, electrical, physical, or optical property (or quality) of an analyte-of-interest. In particular embodiments, the designated reaction is an associative binding event (e.g., incorporation of a fluorescently labeled biomolecule with the analyte-of-interest). The designated reaction can be a dissociative binding event (e.g., release of a fluorescently labeled biomolecule from an analyte-of-interest). The designated reaction may be a chemical transformation, chemical change, or chemical interaction. The designated reaction may also be a change in electrical properties. For example, the designated reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The designated reaction can also be addition or elimination of a proton, for example, detectable as a change in pH of a surrounding solution or environment. An additional designated reaction can be detecting the flow of ions across a membrane (e.g., natural or synthetic bilayer membrane), for example as ions flow through a membrane the current is disrupted and the disruption can be detected. Field sensing of charged tags can also be used as can thermal sensing and other analytical sensing techniques known in the art.

In particular embodiments, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" includes any substance that may be used to obtain a designated reaction. For example, reaction components include reagents, catalysts such as enzymes, reactants for the reaction, samples, products of the reaction, other biomolecules, salts, metal cofactors, chelating agents, and buffer solutions (e.g., hydrogenation buffer). The reaction components may be delivered, individually in solutions or combined in one or more mixture, to various locations in a fluidic network. For instance, a reaction component may be delivered to a reaction chamber where the biological sample is immobilized. The reaction components may interact directly or indirectly with the biological sample. In some embodiments, the removable cartridge 104 is pre-loaded with one or more of the reaction components that are necessary for carrying out a designated assay protocol. Preloading can occur at one location (e.g. a manufacturing facility) prior to receipt of the cartridge 104 by a user (e.g. at a customer's facility).

In some embodiments, the base instrument 102 may be configured to interact with one removable cartridge 104 per session. After the session, the removable cartridge 104 may be replaced with another removable cartridge 104. In other embodiments, the base instrument 102 may be configured to interact with more than one removable cartridge 104 per session. As used herein, the term "session" includes performing at least one of sample preparation and/or biochemical analysis protocol. Sample preparation may include separating, isolating, modifying and/or amplifying one or more components of the biological sample so that the prepared biological sample is suitable for analysis. In some embodiments, a session may include continuous activity in which a number of controlled reactions are conducted until (a) a designated number of reactions have been conducted, (b) a designated number of events have been detected, (c) a designated period of system time has elapsed, (d) signal-to-noise has dropped to a designated threshold; (e) a target component has been identified; (f) system failure or malfunction has been detected; and/or (g) one or more of the resources for conducting the reactions has depleted. Alternatively, a session may include pausing system activity for a period of time (e.g., minutes, hours, days, weeks) and later completing the session until at least one of (a)-(g) occurs.

An assay protocol may include a sequence of operations for conducting the designated reactions, detecting the designated reactions, and/or analyzing the designated reactions. Collectively, the removable cartridge 104 and the base instrument 102 may include the components that are necessary for executing the different operations. The operations of an assay protocol may include fluidic operations, thermal-control operations, detection operations, and/or mechanical operations. A fluidic operation includes controlling the flow of fluid (e.g., liquid or gas) through the system 100, which may be actuated by the base instrument 102 and/or by the removable cartridge 104. For example, a fluidic operation may include controlling a pump to induce flow of the biological sample or a reaction component into a reaction chamber. A thermal-control operation may include controlling a temperature of a designated portion of the system 100. By way of example, a thermal-control operation may include raising or lowering a temperature of a polymerase chain reaction (PCR) zone where a liquid that includes the biological sample is stored. A detection operation may include controlling activation of a detector or monitoring activity of the detector to detect predetermined properties, qualities, or characteristics of the biological sample. As one example, the detection operation may include capturing images of a designated area that includes the biological sample to detect fluorescent emissions from the designated area. The detection operation may include controlling a light source to illuminate the biological sample or controlling a detector to observe the biological sample. A mechanical operation may include controlling a movement or position of a designated component. For example, a mechanical operation may include controlling a motor to move a valve-control component in the base instrument 102 that operably engages a movable valve in the removable cartridge 104. In some cases, a combination of different operations may occur concurrently. For example, the detector may capture images of the reaction chamber as the pump controls the flow of fluid through the reaction chamber. In some cases, different operations directed toward different biological samples may occur concurrently. For instance, a first biological sample may be undergoing amplification (e.g., PCR) while a second biological sample may be undergoing detection.

Similar or identical fluidic elements (e.g., channels, ports, reservoirs, etc.) may be labeled differently to more readily distinguish the fluidic elements. For example, ports may be referred to as reservoir ports, supply ports, network ports, feed port, etc. It is understood that two or more fluidic elements that are labeled differently (e.g., reservoir channel, sample channel, flow channel, bridge channel) do not require that the fluidic elements be structurally different. Moreover, the claims may be amended to add such labels to more readily distinguish such fluidic elements in the claims.

A "liquid," as used herein, is a substance that is relatively incompressible and has a capacity to flow and to conform to a shape of a container or a channel that holds the substance. A liquid may be aqueous based and include polar molecules exhibiting surface tension that holds the liquid together. A liquid may also include non-polar molecules, such as in an oil-based or non-aqueous substance. It is understood that references to a liquid in the present application may include a liquid that was formed from the combination of two or more liquids. For example, separate reagent solutions may be later combined to conduct designated reactions.

The removable cartridge 104 is configured to separably engage or removably couple to the base instrument 102. As used herein, when the terms "separably engaged" or "removably coupled" (or the like) are used to describe a relationship between a removable cartridge and a base instrument, the term is intended to mean that a connection between the removable cartridge and the base instrument is readily separable without destroying the base instrument. Accordingly, the removable cartridge may be separably engaged to the base instrument in an electrical manner such that the electrical contacts of the base instrument are not destroyed. The removable cartridge may be separably engaged to the base instrument in a mechanical manner such that features of the base instrument that hold the removable cartridge are not destroyed. The removable cartridge may be separably engaged to the base instrument in a fluidic manner such that the ports of the base instrument are not destroyed. The base instrument is not considered to be "destroyed," for example, if only a simple adjustment to the component (e.g., realigning) or a simple replacement (e.g., replacing a nozzle) is required. Components (e.g., the removable cartridge 104 and the base instrument 102) may be readily separable when the components can be separated from each other without undue effort or a significant amount of time spent in separating the components. In some embodiments, the removable cartridge 104 and the base instrument 102 may be readily separable without destroying either the removable cartridge 104 or the base instrument 102.

In some embodiments, the removable cartridge 104 may be permanently modified or partially damaged during a session with the base instrument 102. For instance, containers holding liquids may include foil covers that are pierced to permit the liquid to flow through the system 100. In such embodiments, the foil covers may be damaged such that it may be necessary to replace the damaged container with another container. In particular embodiments, the removable cartridge 104 is a disposable cartridge such that the removable cartridge 104 may be replaced and optionally disposed after a single use.

In other embodiments, the removable cartridge 104 may be used for more than one session while engaged with the base instrument 102 and/or may be removed from the base instrument 102, reloaded with reagents, and re-engaged to the base instrument 102 to conduct additional designated reactions. Accordingly, the removable cartridge 104 may be refurbished in some cases such that the same removable cartridge 104 may be used with different consumables (e.g., reaction components and biological samples). Refurbishing can be carried out at a manufacturing facility after the cartridge has been removed from a base instrument located at a customer's facility.

As shown in FIG. 1, the removable cartridge 104 includes a fluidic network 106 that may hold and direct fluids (e.g., liquids or gases) therethrough. The fluidic network 106 includes a plurality of interconnected fluidic elements that are capable of storing a fluid and/or permitting a fluid to flow therethrough. Non-limiting examples of fluidic elements include channels, ports of the channels, cavities, storage modules, reservoirs of the storage modules, reaction chambers, waste reservoirs, detection chambers, multipurpose chambers for reaction and detection, and the like. The fluidic elements may be fluidically coupled to one another in a designated manner so that the system 100 is capable of performing sample preparation and/or analysis.

As used herein, the term "fluidically coupled" (or like term) refers to two spatial regions being connected together such that a liquid or gas may be directed between the two spatial regions. In some cases, the fluidic coupling permits a fluid to be directed back and forth between the two spatial regions. In other cases, the fluidic coupling is uni-directional such that there is only one direction of flow between the two spatial regions. For example, an assay reservoir may be fluidically coupled with a channel such that a liquid may be transported into the channel from the assay reservoir. However, in some embodiments, it may not be possible to direct the fluid in the channel back to the assay reservoir. In particular embodiments, the fluidic network 106 is configured to receive a biological sample and direct the biological sample through sample preparation and/or sample analysis. The fluidic network 106 may direct the biological sample and other reaction components to a waste reservoir.

One or more embodiments may include retaining the biological sample (e.g., template nucleic acid) at a designated location where the biological sample is analyzed. As used herein, the term "retained," when used with respect to a biological sample, includes substantially attaching the biological sample to a surface or confining the biological sample within a designated space. As used herein, the term "immobilized," when used with respect to a biological sample, includes substantially attaching the biological sample to a surface in or on a solid support. Immobilization may include attaching the biological sample at a molecular level to the surface. For example, a biological sample may be immobilized to a surface of a substrate using adsorption techniques including non-covalent interactions (e.g., electrostatic forces, van der Waals, and dehydration of hydrophobic interfaces) and covalent binding techniques where functional groups or linkers facilitate attaching the biological sample to the surface. Immobilizing a biological sample to a surface of a substrate may be based upon the properties of the surface of the substrate, the liquid medium carrying the biological sample, and the properties of the biological sample itself. In some cases, a substrate surface may be functionalized (e.g., chemically or physically modified) to facilitate immobilizing the biological sample to the substrate surface. The substrate surface may be first modified to have functional groups bound to the surface. The functional groups may then bind to the biological sample to immobilize the biological sample thereon. In some cases, a biological sample can be immobilized to a surface via a gel, for example, as described in US Patent Publ. Nos. 2011/0059865 A1 and 2014/0079923 A1, each of which is incorporated herein by reference in its entirety.

In some embodiments, nucleic acids can be immobilized to a surface and amplified using bridge amplification. Useful bridge amplification methods are described, for example, in U.S. Pat. No. 5,641,658; WO 07/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid. In some embodiments, the biological sample may be confined within a predetermined space with reaction components that are configured to be used during amplification of the biological sample (e.g., PCR).

One or more embodiments set forth herein may be configured to execute an assay protocol that is or includes an amplification (or PCR) protocol. During the amplification protocol, a temperature of the biological sample within a reservoir or channel may be changed in order to amplify the biological sample (e.g., DNA of the biological sample). By way of example, the biological sample may experience (1) a pre-heating stage of about 95° C. for about 75 seconds; (2) a denaturing stage of about 95° C. for about 15 seconds; (3) an annealing-extension stage of about of about 59° C. for about 45 seconds; and (4) a temperature holding stage of about 72° C. for about 60 seconds. Embodiments may execute multiple amplification cycles. It is noted that the above cycle describes only one particular embodiment and that alternative embodiments may include modifications to the amplification protocol.

The methods and systems set forth herein can use arrays having features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher. The methods and apparatus set forth herein can include detection components or devices having a resolution that is at least sufficient to resolve individual features at one or more of these exemplified densities.

In the illustrated embodiment, the removable cartridge 104 includes a cartridge housing 110 having a plurality of housing sides 111-114. The housing sides 111-114 include non-mating sides 111-113 and a mating side 114. The mating side 114 is configured to engage the base instrument 102. In the illustrated embodiment, the cartridge housing 110 forms a substantially unitary structure. In alternative embodiments, the cartridge housing 110 may be constructed by one or more sub-components that are combined by a user of the system 100. The sub-components may be combined before the removable cartridge 104 is separably engaged to the base instrument 102 or after one of the sub-components is separably engaged to the base instrument 102. For example, a storage module 150 may be held by a first sub-housing (not shown) and a remainder of the removable cartridge 104 (e.g., fluidic network and imaging device) may include a second sub-housing (not shown). The first and second sub-housings may be combined to form the cartridge housing 110.

The fluidic network 106 is held by the cartridge housing 110 and includes a plurality of sample ports 116 that open to the non-mating side 112. In alternative embodiments, the sample ports 116 may be located along the non-mating sides 111 or 113 or may be located along the mating side 114. Each of the sample ports 116 is configured to receive a biological sample. By way of example only, the biological sample may be whole blood or saliva. In some embodiments, the biological sample may be nucleic acids and other materials (e.g., reagents, buffers, etc.) for conducting PCR. Although three sample ports 116 are shown in FIG. 1, embodiments may include only one sample port, two sample ports, or more than three sample ports.

The fluidic network 106 also includes a fluidic-coupling port 118 that opens to the mating side 114 and is exposed to an exterior of the cartridge housing 110. The fluidic-coupling port 118 is configured to fluidically couple to a system pump 119 of the base instrument 102. The fluidic-coupling port 118 is in flow communication with a pump channel 133 that is part of the fluidic network 106. During operation of the system 100, the system pump 119 is configured to provide a negative pressure for inducing a flow of fluid through the pump channel 133 and through a remainder of the fluidic network 106. For example, the system pump 119 may induce flow of the biological sample from the sample port 116 to a sample-preparation region 132, wherein the biological sample may be prepared for subsequent analysis. The system pump 119 may induce flow of the biological sample from the sample-preparation region 132 to a reaction chamber 126, wherein detection operations are conducted to obtain data (e.g., imaging data) of the biological sample. The system pump 119 may also induce flow of fluid from reservoirs 151, 152 of a storage module 150 to the reaction chamber 126. After the detection operations are conducted, the system pump 119 may induce flow of the fluid into a waste reservoir 128.

In addition to the fluidic network 106, the removable cartridge 104 may include one or more mechanical interfaces 117 that may be controlled by the base instrument 102. For example, the removable cartridge 104 may include a valve assembly 120 having a plurality of flow-control valves 121-123 that are operably coupled to the fluidic network 106. Each of the flow-control valves 121-123 may represent a mechanical interface 117 that is controlled by the base instrument 102. For instance, the flow-control valves 121-123 may be selectively activated or controlled by the base instrument 102, in conjunction with selective activation of the system pump 119, to control a flow of fluid within the fluidic network 106.

For example, in the illustrated embodiment, the fluidic network 106 includes a sample channel 131 that is immediately downstream from and in flow communication with the sample ports 116. Only a single sample channel 131 is shown in FIG. 1, but alternative embodiments may include multiple sample channels 131. The sample channel 131 may include the sample-preparation region 132. The valve assembly 120 includes a pair of channel valves 121, 122, which may also be referred to as flow-control valves. The channel valves 121, 122 may be selectively activated by the base instrument 102 to impede or block flow of the fluid through the sample channel 131. In particular embodiments, the channel valves 121, 122 may be activated to form a seal that retains a designated volume of liquid within the sample-preparation region 132 of the sample channel 131. The designated volume within the sample-preparation region 132 may include the biological sample.

The valve assembly 120 may also include a movable valve 123. The movable valve 123 has a valve body 138 that may include at least one flow channel 140 that extends between corresponding ports. The valve body 138 is capable of moving between different positions to align the ports with corresponding ports of the fluidic network 106. For example, a position of the movable valve 123 may determine the type of fluid that flows into the reaction chamber 126. In a first position, the movable valve 123 may align with a corresponding port of the sample channel 131 to provide the biological sample to the reaction chamber 126. In a second position, the movable valve 123 may align with one or more corresponding ports of reservoir channels 161, 162 that are in flow communication with the reservoirs 151, 152, respectively, of the storage module 150. Each reservoir 151, 152 is configured to store a reaction component that may be used to conduct the designated reactions. The reservoir channels 161, 162 are located downstream from and in flow communication with the reservoirs 151, 152, respectively. In some embodiments, the movable valve 123 may move, separately, to different positions to align with the corresponding ports of the reservoir channels.

In the illustrated embodiment, the movable valve 123 is a rotary valve (or rotatable valve) that is configured to rotate about an axis 142. The movable valve 123 may be similar to the rotary valve 216 (shown FIG. 2). However, it should be understood that alternative embodiments may include movable valves that do not rotate to different positions. In such embodiments, the movable valve may slide in one or more linear directions to align the corresponding ports. Rotary valves and linear-movement valves set forth herein may be similar to the apparatuses described in International Application No. PCT/US2013/032309, filed on Mar. 15, 2013, which is incorporated herein by reference in its entirety.

In some embodiments, the biological sample is illuminated by a light source 158 of the base instrument 102. Alternatively, the light source 158 may be incorporated with the removable cartridge 104. For example, the biological sample may include one or more fluorophores that provide light emissions when excited by a light having a suitable wavelength. In the illustrated embodiment, the removable cartridge 104 has an optical path 154. The optical path 154 is configured to permit illumination light 156 from the light source 158 of the base instrument 102 to be incident on the biological sample within the reaction chamber 126. Thus, the reaction chamber may have one or more optically transparent sides or windows. The optical path 154 may include one or more optical elements, such as lenses, reflectors, fiber-optic lines, and the like, that actively direct the illumination light 156 to the reaction chamber 126. In an exemplary embodiment, the light source 158 may be a light-emitting diode (LED). However, in alternative embodiments, the light source 158 may include other types of light-generating devices, such as lasers or lamps.

In some embodiments, the detection assembly 108 includes an imaging detector 109 and the reaction chamber 126. The imaging detector 109 is configured to detect designated reactions within the reaction chamber 126. In some embodiments, the imaging detector 109 may be positioned relative to the reaction chamber 126 to detect light signals (e.g., absorbance, reflection/refraction, or light emissions) from the reaction chamber 126. The imaging detector 109 may include one or more imaging devices, such as a charge-coupled device (CCD) camera or complementary-metal-oxide semiconductor (CMOS) imager. In some embodiments, the imaging detector 109 may detect light signals that are emitted from chemiluminescence. Yet still in other embodiments, the detection assembly 108 may not be limited to imaging applications. For example, the detection assembly 108 may be one or more electrodes that detect an electrical property of a liquid.

As set forth herein, the base instrument 102 is configured to operably engage the removable cartridge 104 and control various operations within the removable cartridge 104 to conduct the designated reactions and/or obtain data of the biological sample. To this end, the mating side 114 is configured to permit or allow the base instrument 102 to control operation of one or more components of the removable cartridge 104. For example, the mating side 114 may include a plurality of access openings 171-173 that permit the valves 121-123 to be controlled by the base instrument 102. The mating side 114 may also include an access opening 174 that is configured to receive a thermocycler 186 (e.g., thermal or heat-transfer block) of the base instrument 102. In the illustrated embodiment, the thermocycler 186 is a thermal block. The access opening 174 extends along the sample channel 131. As shown, the access openings 171-174 open to the mating side 114.

In some embodiments, the fluidic network 106 and the valve assembly 123 may constitute a flow-control system 164. The flow-control system 164 may include the components that cooperate to control the flow of one or more fluids through the system 100 or, more specifically, the removable cartridge 104 in order to execute one or more designated operations. The flow-control system 164 may include additional components, such as the system pump 119, in other embodiments. The flow-control system 164 may be similar or identical to the flow-control system 200 (shown in FIG. 2).

The base instrument 102 has a control side 198 configured to separably engage the mating side 114 of the removable cartridge 104. The mating side 114 of the removable cartridge 104 and the control side 198 of the base instrument 102 may collectively define a system interface 195. The system interface 195 represents a common boundary between the removable cartridge 104 and the base instrument 102 through which the base instrument 102 and the removable cartridge 104 are operably engaged. More specifically, the base instrument 102 and the removable cartridge 104 are operably engaged along the system interface 195 such that the base instrument 102 may control various features of the removable cartridge 104 through the mating side 114. For instance, the base instrument 102 may have one or more controllable components that control corresponding components of the removable cartridge 104.

In some embodiments, the base instrument 102 and the removable cartridge 104 are operably engaged such that the base instrument 102 and the removable cartridge 104 are secured to each other at the system interface 195 with at least one of an electric coupling, thermal coupling, optical coupling, valve coupling, or fluidic coupling established through the system interface 195. In the illustrated embodiment, the base instrument 102 and the removable cartridge 104 are configured to have an electric coupling, a thermal coupling, a valve coupling, and an optical coupling. More specifically, the base instrument 102 and the removable cartridge 104 may communicate data and/or electrical power through the electric coupling. The base instrument 102 and the removable cartridge 104 may convey thermal energy to and/or from each other through the thermal coupling, and the base instrument 102 and the removable cartridge 104 may communicate light signals (e.g., the illumination light) through the optical coupling.

In the illustrated embodiment, the system interface 195 is a single-sided interface 195. For example, the control side 198 and the housing side 114 are generally planar and face in opposite directions. The system interface 195 is single-sided such that that the removable cartridge 104 and the base instrument 102 are operably coupled to each other only through the mating side 114 and the control side 198. In alternative embodiments, the system interface may be a multi-sided interface. For example, at least 2, 3, 4, or 5 sides of a removable cartridge may be mating sides that are configured to couple with a base instrument. The multiple sides may be planar and may be arranged orthogonally or opposite each other (e.g. surrounding all or part of a rectangular volume).

To control operations of the removable cartridge 104, the base instrument 102 may include valve actuators 181-183 that are configured to operably engage the flow-control valves 121-123, a thermocycler 186 that is configured to provide and/or remove thermal energy from the sample-preparation region 132, and a contact array 188 of electrical contacts. The base instrument 102 may also include the light source 158 positioned along the control side 198. The base instrument 102 may also include the system pump 119 having a control port 199 positioned along the control side 198.

The system 100 may also include a locking mechanism 176. In the illustrated embodiment, the locking mechanism 176 includes a rotatable latch 177 that is configured to engage a latch-engaging element 178 of the removable cartridge 104. Alternatively, the removable cartridge 104 may include the rotatable latch 177 and the base instrument 102 may include the latch-engaging element 178. When the removable cartridge 104 is mounted to the base instrument 102, the latch 177 may be rotated and engage the latching-engaging element 178. A camming effect generated by the locking mechanism 176 may urge or drive the removable cartridge 104 toward the base instrument 102 to secure the removable cartridge 104 thereto.

The base instrument 102 may include a user interface 125 that is configured to receive user inputs for conducting a designated assay protocol and/or configured to communicate information to the user regarding the assay. The user interface 125 may be incorporated with the base instrument 102. For example, the user interface 125 may include a touchscreen that is attached to a housing of the base instrument 102 and configured to identify a touch from the user and a location of the touch relative to information displayed on the touchscreen. Alternatively, the user interface 125 may be located remotely with respect to the base instrument 102.

The base instrument 102 may also include a system controller 180 that is configured to control operation of at least one of the valve actuators 181-183, the thermocycler 186, the contact array 188, the light source 158, or the system pump 119. The system controller 180 is illustrated conceptually as a collection of circuitry modules, but may be implemented utilizing any combination of dedicated hardware boards, DSPs, processors, etc. Alternatively, the system controller 180 may be implemented utilizing an off-the-shelf PC with a single processor or multiple processors, with the functional operations distributed between the processors. As a further option, the circuitry modules described below may be implemented utilizing a hybrid configuration in which certain modular functions are performed utilizing dedicated hardware, while the remaining modular functions are performed utilizing an off-the-shelf PC and the like.

The system controller 180 may include a plurality of circuitry modules 190-193 that are configured to control operation of certain components of the base instrument 102 and/or the removable cartridge 104. For instance, the circuitry module 190 may be a flow-control module 190 that is configured to control flow of fluids through the fluidic network 106. The flow-control module 190 may be operably coupled to the valve actuators 181-183 and the system pump 119. The flow-control module 190 may selectively activate the valve actuators 181-183 and the system pump 119 to induce flow of fluid through one or more paths and/or to block flow of fluid through one or more paths.

By way of example only, the valve actuator 183 may rotatably engage the movable valve 123. The valve actuator 183 may include a rotating motor 189 that is configured to drive (e.g., rotate) the valve actuator 183. The flow-control module 190 may activate the valve actuator 183 to move the movable valve 123 to a first rotational position. With the movable valve 123 in the first rotational position, the flow-control module 190 may activate the system pump 119 thereby drawing the biological sample from the sample-preparation region 132 and into the reaction chamber 126. The flow-control module 190 may then activate the valve actuator 183 to move the movable valve 123 to a second rotational position. With the movable valve 123 in the second rotational position, the flow-control module 190 may activate the system pump 119 thereby drawing one or more of the reaction components from the corresponding reservoir (s) and into the reaction chamber 126. In some embodiments, the system pump 119 may be configured to provide positive pressure such that the fluid is actively pumped in an opposite direction. Such operations may be used to add multiple liquids into a common reservoir thereby mixing the liquids within the reservoir. Accordingly, the fluidic-coupling port 118 may permit fluid (e.g., gas) to exit the cartridge housing 110 or may receive fluid into the cartridge housing 110.

The system controller 180 may also include a thermal-control module 191. The thermal-control module 191 may control the thermocycler 186 to provide and/or remove thermal energy from the sample-preparation region 132. In one particular example, the thermocycler 186 may increase and/or decrease a temperature that is experienced by the biological sample within the sample channel 131 in accordance with a PCR protocol. Although not shown, the system 100 may include additional thermal devices that are positioned adjacent to the sample-preparation region 132.

The system controller 180 may also include a detection module 192 that is configured to control the detection assembly 108 to obtain data regarding the biological sample. The detection module 192 may control operation of the detection assembly 108 through the contact array 188. For example, the detection assembly 108 may be communicatively engaged to a contact array 194 of electrical contacts 196 along the mating side 114. In some embodiment, the electrical contacts 196 may be flexible contacts (e.g., pogo contacts or contact beams) that are capable of repositioning to and from the mating side 114. The electrical contacts 196 are exposed to an exterior of the cartridge housing and are electrically coupled to the detection assembly 108. The electrical contacts 196 may be referenced as input/output (I/O) contacts. When the base instrument 102 and the removable cartridge 104 are operably engaged, the detection module 192 may control the detection assembly 108 to obtain data at predetermined times or for predetermined time periods. By way of example, the detection module 192 may control the detection assembly 108 to capture an image of the reaction chamber 126 when the biological sample has a fluorophore attached thereto. A number of images may be obtained.

Optionally, the system controller 180 includes an analysis module 193 that is configured to analyze the data to provide at least partial results to a user of the system 100. For example, the analysis module 193 may analyze the imaging data provided by the imaging detector 109. The analysis may include identifying a sequence of nucleic acids of the biological sample.

The system controller 180 and/or the circuitry modules 190-193 may include one or more logic-based devices, including one or more microcontrollers, processors, reduced instruction set computers (RISC), application specific integrated circuits (ASICs), field programmable gate array (FPGAs), logic circuits, and any other circuitry capable of executing functions described herein. In an exemplary embodiment, the system controller 180 and/or the circuitry modules 190-193 execute a set of instructions that are stored therein in order to perform one or more assay protocols. Storage elements may be in the form of information sources or physical memory elements within the base instrument 102 and/or the removable cartridge 104. The protocols performed by the assay system 100 may be to carry out, for example, quantitative analysis of DNA or RNA, protein analysis, DNA sequencing (e.g., sequencing-by-synthesis (SBS)), sample preparation, and/or preparation of fragment libraries for sequencing.

The set of instructions may include various commands that instruct the system 100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the system 100, processed in response to user inputs, or processed in response to a request made by another processing machine (e.g., a remote request through a communication link).

The system controller 180 may be connected to the other components or sub-systems of the system 100 via communication links, which may be hardwired or wireless. The system controller 180 may also be communicatively connected to off-site systems or servers. The system controller 180 may receive user inputs or commands, from a user interface (not shown). The user interface may include a keyboard, mouse, a touch-screen panel, and/or a voice recognition system, and the like.

The system controller 180 may serve to provide processing capabilities, such as storing, interpreting, and/or executing software instructions, as well as controlling the overall operation of the system 100. The system controller 180 may be configured and programmed to control data and/or power aspects of the various components. Although the system controller 180 is represented as a single structure in FIG. 1, it is understood that the system controller 180 may include multiple separate components (e.g., processors) that are distributed throughout the system 100 at different locations. In some embodiments, one or more components may be integrated with a base instrument and one or more components may be located remotely with respect to the base instrument.

Figure 2:
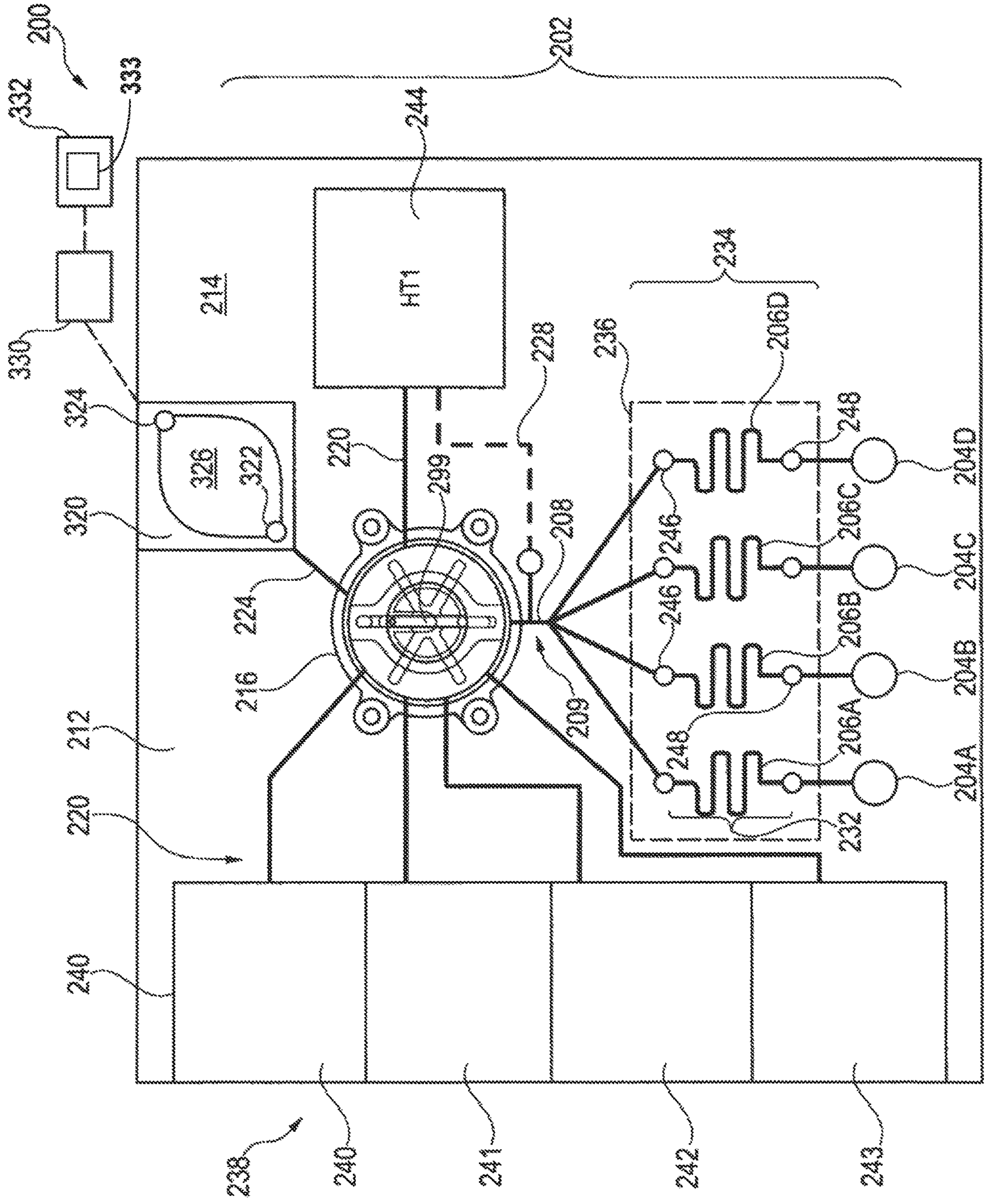
FIG. 2 is a plan view of a flow-control system formed in accordance with an embodiment that may be used with the system of FIG. 1.

FIG. 2 is a plan view of a flow-control system 200 formed in accordance with an embodiment. The flow-control system 200 may be part of a system (not shown) for sample preparation and/or sample analysis, such as the system 100 (shown in FIG. 1). In some embodiments, the flow-control system 200 is entirely within an integrated device, such as the removable cartridge 104 (FIG. 1). In other embodiments, however, the flow-control system 200 may be part of a standard system (e.g., desktop system). In FIG. 2, components of the flow-control system 200 are located within a localized area. In other embodiments, the components of the flow-control system 200 may be separated from each other and distributed in different areas.

In the illustrated embodiment, the flow-control system 200 includes a fluidic network 202 that is configured to have one or more fluids (e.g., gas or liquid) flow therethrough. The fluidic network 202 includes an arrangement of interconnected fluidic elements. The fluidic elements may be configured to direct fluid to designated regions within the fluidic network 202 where, for example, the fluid may be subjected to predetermined conditions and/or undergo designated reactions. The fluidic elements may be selectively interconnected by one or more valves such that one or more fluidic elements may be disconnected with respect to one or more other fluidic elements during operation.

In the illustrated embodiment, the fluidic network 202 includes sample ports 204A-204D and sample channels 206A-206D that are in flow communication with the sample ports 204A-204D, respectively. The sample channels 206A-206D extend from the corresponding sample ports 204A-204D to a common junction or intersection 209. The fluidic network 202 also includes a combined sample channel 208 that extends from the junction 209 to a supply port 210 (shown in FIG. 9). A rotary valve 216 is located over the supply port 210.

The fluidic network 202 also includes a feed port 226 (shown in FIG. 9) and a feed channel 224 that extends from the feed port 226. The feed channel 224 extends between the feed port 226 and a flow cell 320 of the fluidic network 202. The flow cell 320 includes an inlet port 322, an outlet port 324, and a reaction chamber 326 extending therebetween. During operation, the fluid may flow from the feed channel 224 through the inlet port 322 and exit the reaction chamber 326 through the outlet port 324. After exiting the reaction chamber 326, the fluid may flow to a waste reservoir 330 of the fluidic network 202. The waste reservoir 330 is represented by a small box in FIG. 2, but it should be understood that the volume of the waste reservoir 330 may be larger than, for example, the reservoirs 240-244.

While the fluid flows through the reaction chamber 326, the fluid may interact with existing material (e.g., analytes) within the reaction chamber 326. Designated reactions may be detected within the reaction chamber 326. For example, a detection assembly (not shown) may be positioned adjacent to the reaction chamber 326 and detect light signals from the reaction chamber 326.

In the illustrated embodiment, the sample ports 204A-204D open to a body side or surface 214 of the microfluidic body 212 such that the sample ports 204A-204D are exposed to an exterior of the microfluidic body 212. The sample channels 206A-206D and the combined sample channel 208 extend through (e.g., within) the microfluidic body 212. The supply port 210 may open to the body side 214. Alternatively, the supply port 210 may open to an underside (not shown) or a lateral side of the microfluidic body 212. Accordingly, the sample channels 206A-206D are in flow communication with a single port, such as the supply port 210. In alternative embodiments, however, the sample channels 206A-206D may be in flow communication with separate supply ports that open to the body side 214. In such alternative embodiments, each sample channel may extend between a respective sample port and a respective supply port.

In the illustrated embodiment, the fluidic network 202 also includes a plurality of reservoir channels 220. Each of the reservoir channels 220 is fluidically interposed between a reservoir port 222 (shown in FIG. 10) and a reservoir 240. The reservoir ports 222 open to the body side 214. Similar to the supply port 210, the reservoir ports 222 may be covered by the rotary valve 216. Optionally, the fluidic network 202 may include a reservoir channel 228 that is fluidically interposed between the common sample channel 208 and a reservoir 230.

In the illustrated embodiment, the flow-control system 200 includes a microfluidic body 212. The microfluidic body 212 may be a physical structure that defines the fluidic elements of the fluidic network 202. For example, the microfluidic body 212 may include stacked PCB layers in which one or more of the layers are etched or shaped to form one or more of the channels (e.g., the sample channels 206A-206D, the common sample channel 208, the reservoir channels 220, 228, and the feed channel 224) and one or more of the ports (e.g., the sample ports 204A-204D, the reservoir ports 222, the supply port 210, and the feed port 226) of the fluidic network 202. The flow cell 320 may be secured to the microfluidic body 212. Such microfluidic bodies are illustrated and described in U.S. Provisional Application No. 62/003,264 and U.S. Provisional Application No. 61/951,462. Each of these provisional applications is incorporated herein by reference in its entirety. Alternatively or in addition to PCB layers, other materials may be used, such as glass or plastic. In alternative embodiments, the microfluidic body 212 may be collectively formed from multiple body components. In some cases, the fluidic network 202 is at least partially formed by tubing.

The rotary valve 216 is configured to rotate about an axis 299 to different valve positions (e.g., rotational positions) to fluidically couple different channels of the fluidic network 202. The rotary valve 216 may be slidably coupled to the body side 214 and may be positioned to cover a number of ports that open to the body side 214, such as the reservoir ports 222, the supply port 210, and the feed port 226. The rotary valve 216 includes at least one flow channel 218 (shown in FIG. 9) that is configured to fluidically connect discrete channels. For example, when the rotary valve 216 is in a first valve position, the flow channel 218 may fluidically connect the sample channel 208 to the feed channel 224. When the rotary valve 216 is in a second rotational position, the flow channel 218 may fluidically connect one or the reservoir channels 220 to the feed channel 224.

Each of the sample ports 204A-204D is configured to receive a corresponding biological sample. For instance, a user of the flow-control system 200, such as a technician or lab worker, may load (e.g., pipette) a biological sample into one or more of the sample ports 204A-204D. The biological samples may be for the same individual (e.g., human) or may be for multiple different individuals from a population. It should be understood that the biological sample may be from other species, such as animals, plants, bacteria, or fungus. In the illustrated embodiment, the sample ports 204A-204D are configured to be accessed from an exterior of the flow-control system 200. In alternative embodiments, the sample ports 204A-204D may be part of a larger fluidic network such that the biological samples are delivered to the sample ports 204A-204D through the larger fluidic network.

As shown in FIG. 2, each of the sample channels 206A-206D may include a sample-preparation region 232. In the illustrated embodiment, the sample channels 206A-206D have corresponding wavy or serpentine paths along the corresponding sample-preparation region 232. The wavy or serpentine paths may allow a greater volume of the biological sample to exist within a thermal-control area 234. In alternative embodiments, the sample-preparation region 232 may have different dimensions than other portions of the corresponding sample channel. For example, the sample-preparation region 232 may form a wide chamber or a well with an increased depth.

In the sample-preparation region 232, the biological sample may undergo a process to prepare the biological sample for subsequent reactions and/or analysis. For example, the biological sample may experience a change in pressure and/or temperature. Alternatively or in addition to, the biological sample may be mixed with one or more reaction components within the sample-preparation region 232. In some embodiments, the flow-control system 200 may include a thermal-control strip or band 236 (indicated by a dashed line) that extends along the thermal-control area 234 that is adjacent to the sample-preparation regions 232 of the sample channels 206A-206D. In some embodiments, the thermal-control strip 236 may be a flexible PCB heater, such as the flexible PCB heater described in U.S. Provisional Application No. 61/951,462, which is incorporated by reference in its entirety. The flexible PCB heater may extend along the thermal-control area 234 and have conductive traces therein that generate heat when a current is permitted to flow therethrough.

The thermal-control strip 236 is configured to control a temperature of the biological samples within the corresponding sample channels 206A-206D along the thermal-control area 234. The temperature may be controlled during an amplification protocol in which the biological samples experience an increase/decrease in temperature in accordance with a predetermined schedule in order to amplify the biological sample. In such embodiments, the biological samples may be loaded into the sample ports 204A-204D with an amplification (e.g., PCR) mix of reagents. Alternatively, the amplification mix may be delivered separately to the sample-preparation regions 232 through the fluidic network 202. For example, the sample-preparation regions 232 may be in flow communication with another channel (not shown) through which the amplification mix may be delivered.

In some embodiments, the flow-control system 200 includes a storage assembly or module 238. As shown, the storage assembly 238 includes a plurality of reservoirs 240-244. Each of the reservoirs 240-244 is configured to hold a reaction component that may be used during a predetermined assay protocol (e.g., SBS protocol). Each of the reservoirs 240-244 may be in flow communication with a corresponding port through one of the reservoir channels 220. As described herein, the rotary valve 216 is configured to rotate to different valve positions in accordance with a predetermined schedule to fluidically connect the feed channel 224 to other channels of the fluidic network 202.

In some embodiments, the flow-control system 200 may also include channel valves 246, 248. As shown, each of the sample channels 206A-206D is coupled to a pair of the channel valves 246, 248. The corresponding sample-preparation region 232 for each sample channel 206A-206D extends between the corresponding pair of channel valves 246, 248. Each pair of channel valves 246, 248 is configured to seal the corresponding biological sample within the sample-preparation region 232 as the biological sample experiences different conditions. For example, the channel valves 246, 248 may seal the corresponding biological sample therebetween as the biological sample experiences thermocycling of a PCR protocol.

To induce flow throughout the fluidic network 202, the flow-control system 200 may include a pump assembly 332. In the illustrated embodiment, the flow-control system 200 includes only a single pump 333 that is located downstream from the reaction chamber 326 and draws or sucks the fluid through the fluidic network 202. In alternative embodiments, one or more pumps may be used to push the fluid through the fluidic network 202. For example, one or more pumps may be fluidically positioned upstream with respect to the reservoirs 240-243 and/or the reservoir 244. The sample ports 204A-204D may also be fluidically connected to an upstream pump that induces flow of the biological sample toward the sample channel 208.

Figure 4:
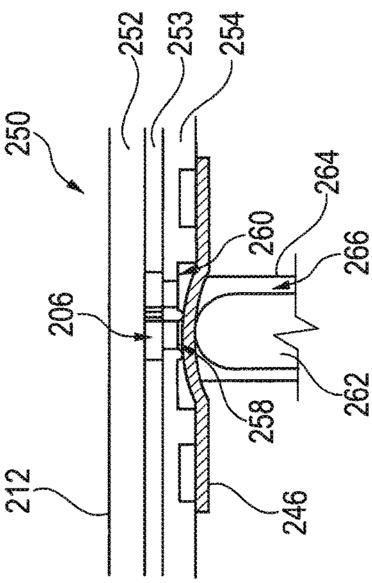
FIG. 4 is a cross-section of a valving mechanism of FIG. 3 in a second state or condition.
Figure 3:
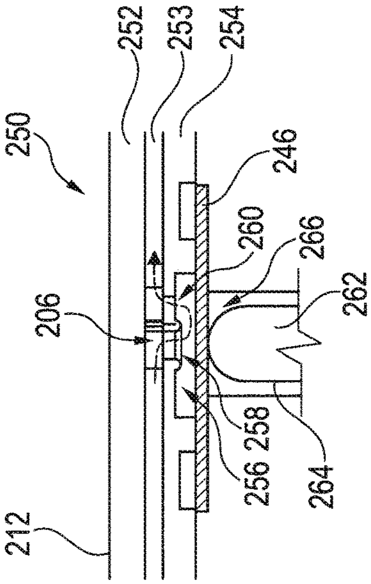
FIG. 3 is a cross-section of a valving mechanism in a first state or condition that may be used with the flow-control system of FIG. 2.

FIGS. 3-8 illustrate different valving mechanisms through which the flow-control system 200 (FIG. 2) may control (e.g., regulate) flow through the fluidic network 202 (FIG. 2). More specifically, FIGS. 3 and 4 illustrate a cross-section of a valving mechanism 250 that includes the channel valve 246. Although the following is with respect to the channel valve 246, the channel valve 248 (FIG. 2) and other valves may include similar or identical features. As shown, the microfluidic body 212 includes a plurality of layers 252-254 that are stacked side-by-side. The layers 252-254 may be printed circuit board (PCB) layers. One or more of the layers 252-254 may be etched such that, when the layers 252-254 are stacked side-by-side, the microfluidic body 212 forms the sample channel 206. The sample channel 206 includes a valve or interior cavity 256.

The channel valve 246 is configured to regulate flow of a fluid through the sample channel 206. For example, the channel valve 246 may permit maximum clearance so that the fluid may flow unimpeded. The channel valve 246 may also impede the flow of fluid therethrough. As used herein, the term "impede" may include slowing the flow of fluid or entirely blocking the flow of fluid. As shown, the sample channel 206 includes first and second ports 258, 260 that are in flow communication with the valve cavity 256. the channel is configured for fluid to flow into the valve cavity 256 through the first port 258 and out of the valve cavity 256 through the second port 260. In the illustrated embodiment, the channel valve 246 constitutes a flexible membrane that is capable of being flexed between first and second conditions. The flexible membrane is in the first condition in FIG. 3 and in the second condition in FIG. 4. In particular embodiments, the flexible membrane is a flexible layer. The flexible layer is configured to be pushed into the valve cavity 256 and cover the first port 258 to block the flow of fluid therethrough. In alternative embodiments, the channel valve 246 may be another physical element that is capable of moving between different conditions or positions to regulate flow of the fluid.

Figure 6:
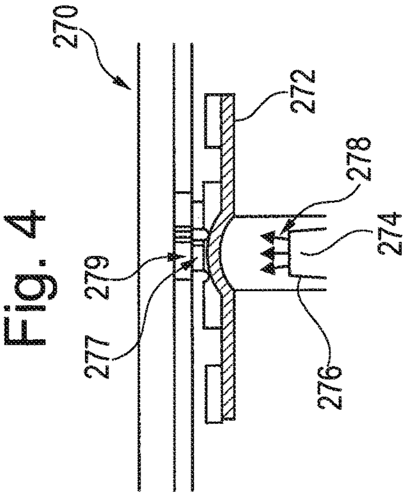
FIG. 6 is a cross-section of a valving mechanism of FIG. 5 in a second state or condition.
Figure 5:
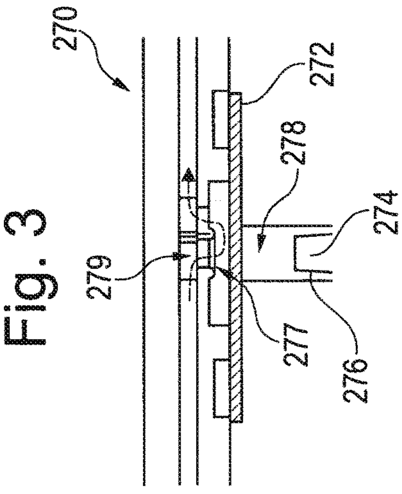
FIG. 5 is a cross-section of a valving mechanism in a first state or condition that may be used with the flow-control system of FIG. 2.

The flow-control system 200 (FIG. 2) may also include a valve actuator 262 that is configured to activate the channel valve 246. For instance, the valve actuator 262 may flex the flexible membrane between the first and second conditions. The valve actuator 262 includes an elongated body 264, such as a post or rod, that extends through an access hole or opening 266. The access hole 266 permits the valve actuator 262 to directly engage the channel valve 246, which is a flexible membrane in the illustrated embodiment. In FIG. 5, the valve actuator 262 is in a first state or position. In FIG. 6, the valve actuator 262 is in a second state or position. In the second position, the valve actuator 262 is engaged with the channel valve 246 and has been moved a distance toward the first port 258. The valve actuator 262 may deform the channel valve 246 such that the channel valve 246 covers the first port 258. As such, fluid flow through the first port 258 is blocked by the channel valve 246.

FIGS. 5 and 6 illustrate a cross-section of a valving mechanism 270 that includes a channel valve 272. In some embodiments, the channel valve 246 (FIG. 2) may be substituted with the channel valve 272. The valving mechanism 270 may be similar to the valving mechanism 250. For example, the valving mechanism includes the channel valve 272 and a valve actuator 274. The valve actuator 274 has an elongated body 276, such as a nozzle, that extends into an access hole or opening 278. The access hole 278 may constitute a closed or sealed chamber. In an exemplary embodiment, the channel valve 272, which may be a flexible membrane, is pneumatically activated by the valve actuator 274. More specifically, the valve actuator 274 is configured to provide a fluid (e.g., air) to increase a pressure within the closed chamber thereby causing the channel valve 272 to deform. When the channel valve 272 is deformed, the channel valve may cover a port 277 of a sample channel 279 thereby blocking flow through the sample channel 279.

Figure 8:
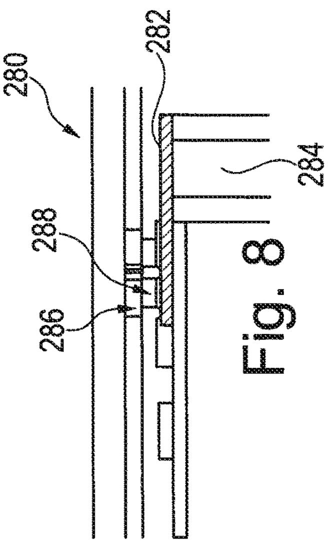
FIG. 8 is a cross-section of a valving mechanism of FIG. 7 in a second state or condition.
Figure 7:
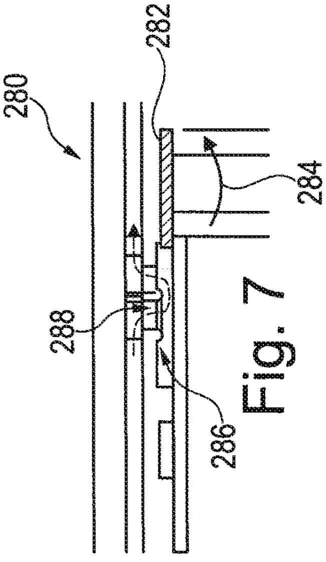
FIG. 7 is a cross-section of a valving mechanism in a first state or condition that may be used with the flow-control system of FIG. 2.

FIGS. 7 and 8 illustrate a valving mechanism 280 that includes a channel valve 282. The valving mechanism 280 may include similar features as the valving mechanisms 250 (FIG. 3), 270 (FIG. 5). The channel valve 282 is rotatably engaged to a valve actuator 284. The channel valve 282 is a planar body that is shaped to permit flow through a sample channel 286 when in a first rotational position (shown in FIG. 7) and block flow through the sample channel 286 when in a second rotational position (shown in FIG. 8). More specifically, the channel valve 282 may cover a port 288 when in the second rotational position.

Figure 9:
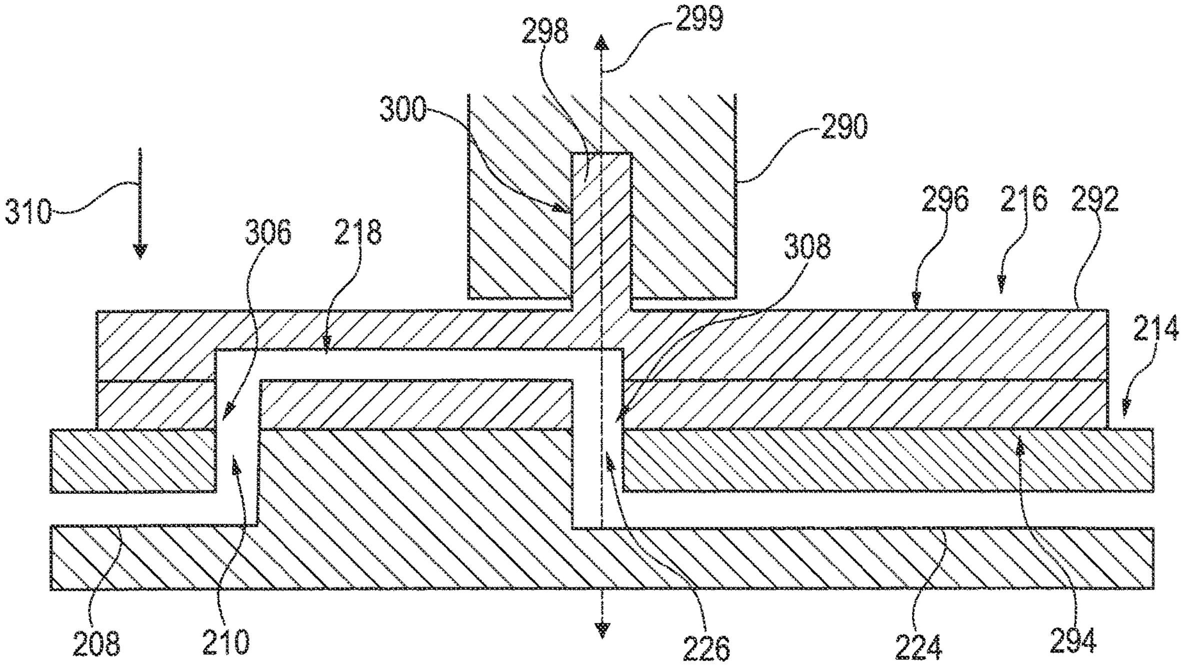
FIG. 9 is a cross-section of a rotary valve mounted to a microfluidic body in accordance with an embodiment.

FIG. 9 illustrates a cross-section of the rotary valve 216 that is operably engaged with a valve actuator 290. The rotary valve 216 is slidably engaged to the body side 214 of the microfluidic body 212. The valve actuator 290 is configured to rotate the rotary valve 216 about the axis 299 to designated valve positions (or rotational positions) to fluidically couple different channels of the fluidic network 202 (FIG. 1). The rotary valve 216 includes a valve body 292 having a fluidic side 294 and an operative side 296. The operative side 296 may include a mechanical interface 298 that is configured to engage the valve actuator 290. In the illustrated embodiment, the mechanical interface 298 includes a planar body or fin that coincides with the axis 299. The valve actuator 290 includes a slot 300 that is configured to receive the mechanical interface 298 such that the valve actuator 290 operably engages the rotary valve 216. More specifically, the valve actuator 290 may engage the rotary valve 216 so that the valve actuator 290 is capable of rotating the rotary valve 216 about the axis 299.

The body side 214 includes the supply port 210 and the feed port 226. The body side 214 also includes the reservoir ports 222A-222E (shown in FIG. 10). The flow channel 218 extends between first and second channel ports 306, 308. The first and second channel ports 306, 308 open to the fluidic side 294 of the valve body 292. In an exemplary embodiment, the rotary valve 216 includes only two channel ports 306, 308 and only one flow channel 218. However, in other embodiments, the rotary valve 216 may include more than two channel ports and/or more than one flow channel. Such embodiments may enable fluidically connecting more than two channels at a single rotational position of the rotary valve 216.

As shown in FIG. 9, the feed port 226 is aligned and fluidically coupled to the channel port 308, and the supply port 210 is aligned and fluidically coupled to the channel port 306. Based on the rotational position of the rotary valve 216, the channel port 306 may also be fluidically coupled to one of the reservoir ports 222A-222E. As noted above, the rotary valve 216 is configured to rotate about the axis 299. In some embodiments, the feed port 226 and the channel port 308 are positioned such that the feed port 226 and the channel port 308 are aligned with the axis 299. More specifically, the axis 299 extends through each of the feed port 226 and the channel port 308.

When the valve actuator 290 is operably engaged to the rotary valve 216, the valve actuator 290 may apply an actuator force 310 in a direction against the body side 214. In such embodiments, the actuator force 310 may be sufficient to seal the flow channel 218 between the channel ports 306, 308 and to seal the reservoir ports 222 and/or the supply port 210.

Accordingly, the rotary valve 216 may fluidically couple the feed port 226 and the supply port 210 at a first rotational position and fluidically couple the feed port 226 and a corresponding reservoir port 222 at a second rotational position. When the rotary valve 216 is rotated between the different rotational positions, the rotary valve 216 effectively changes a flow path of the fluidic network.

The fluid may flow in either direction through the flow channel 218. For example, a system pump (not shown), such as the system pump 119 (FIG. 1) may be in flow communication with the feed port 226. The system pump may generate a suction force that pulls the fluid through the supply port 210 (or a corresponding reservoir port 222) into the flow channel 218 and through the feed port 226. Alternatively, the system pump may provide a positive pressure that displaces fluid within the flow channel 218 such that the fluid flows through the feed port 226 into the flow channel 218 and through the supply port 210 (or a corresponding reservoir port 222).

Figure 10:
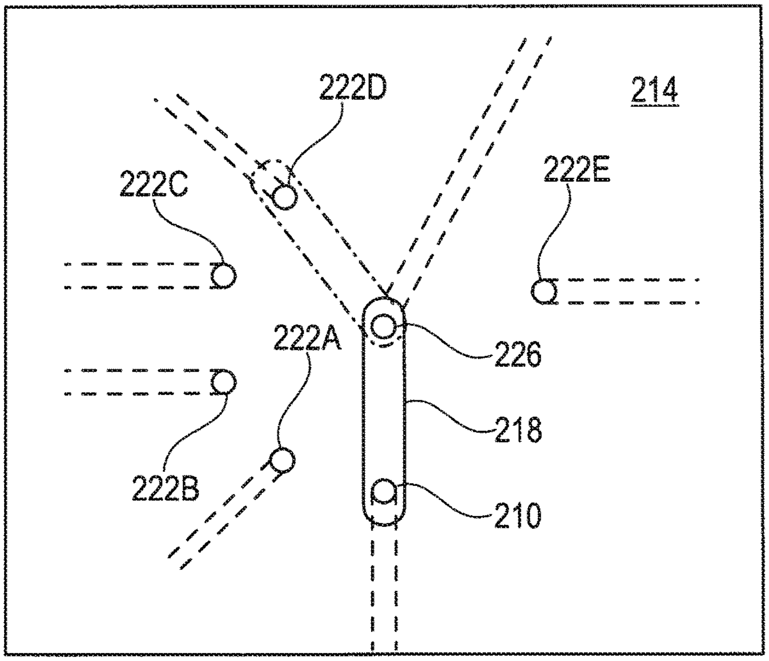
FIG. 10 is a plan view of the microfluidic body of FIG. 9.

FIG. 10 is a top-down view of the body side 214 illustrating the supply port 210, the feed port 226, and reservoir ports 222A-222E. In FIG. 10, the flow channel 218 is represented in two different rotational positions, but it is understood that the flow channel 218 may have other rotational positions. The rotational positions of the flow channel 218 correlate to valve positions of the rotary valve 216 (FIG. 2). The reservoir ports 222A-222E are fluidically coupled to corresponding reservoirs through the corresponding reservoir channel. For example, the reservoir port 222A is fluidically coupled to the reservoir 243; the reservoir port 222B is fluidically coupled to the reservoir 242; the reservoir port 222C is fluidically coupled to the reservoir 241; the reservoir port 222D is fluidically coupled to the reservoir 240; and the reservoir port 222E is fluidically coupled to the reservoir 244. As described above, based on a rotational position of the rotary valve 216 (FIG. 2), the flow channel 218 may fluidically couple the feed port 226 to the supply port 210 or to one of the corresponding reservoir ports 222A-222E.

Table 1 illustrates various stages of a sequencing-by-synthesis (SBS) protocol. In an exemplary embodiment, the reservoir 244 includes a hydrogenation buffer, the reservoir 243 includes a nucleotides solution, the reservoir 242 includes a wash solution, and the reservoir 241 includes a cleaving solution. Although Table 1 provides a schedule for an SBS protocol, it should be understood that various schedules may be provided based on the desired assay protocol. In the following example, the biological samples have been amplified within the corresponding sample-preparation region 232 (FIG. 2) in accordance with a PCR protocol.

At stage 1, the flow channel 218 has a valve position that fluidically couples the supply port 210 and the feed port 226. At stage 1, the channel valves 246, 248 (FIG. 2) that are coupled to the sample channel 206A are deactivated (e.g., in the first condition) to permit a first biological sample to flow through the sample channel 206A and the sample channel 208. The channel valves 246, 248 that are coupled to the sample channels 206B-206D, however, are activated to seal the second, third, and fourth biological samples within the corresponding sample-preparation region 232. Accordingly, at stage 1, the pump assembly 332 (FIG. 2) may induce flow of the first biological sample into the flow channel 218. At stage 2, the rotary valve 216 is rotated to a second valve position, while the first biological sample is stored within the flow channel 218, so that the flow channel 218 fluidically couples the reservoir port 222E and the feed port 226. In the second valve position, the pump assembly 332 may induce a flow of the fluid within the flow channel 218 such that the first biological sample flows through the reservoir port 222E and into the hydrogenation buffer.

At stage 3, the rotary valve 216 is rotated back to the first valve position and the channel valves 246, 248 are selectively activated so that the second biological sample is permitted to flow into the flow channel 218 while the third and fourth biological samples are sealed within the sample-preparation regions 232. At stage 4, the rotary valve 216 is rotated back to the second valve position, while the second biological sample is stored within the flow channel 218, and the second biological sample is added to the hydrogenation buffer with the first biological sample. During stages 5-8, the third and fourth biological samples are removed from the corresponding sample-preparation regions and added to the hydrogenation buffer. Accordingly, four biological samples may be stored within a single reservoir having hydrogenation buffer. While within the reservoir 243, reactions may occur with the biological samples and the hydrogenation buffer that prepare the biological samples for SBS sequencing.

Figure 11:
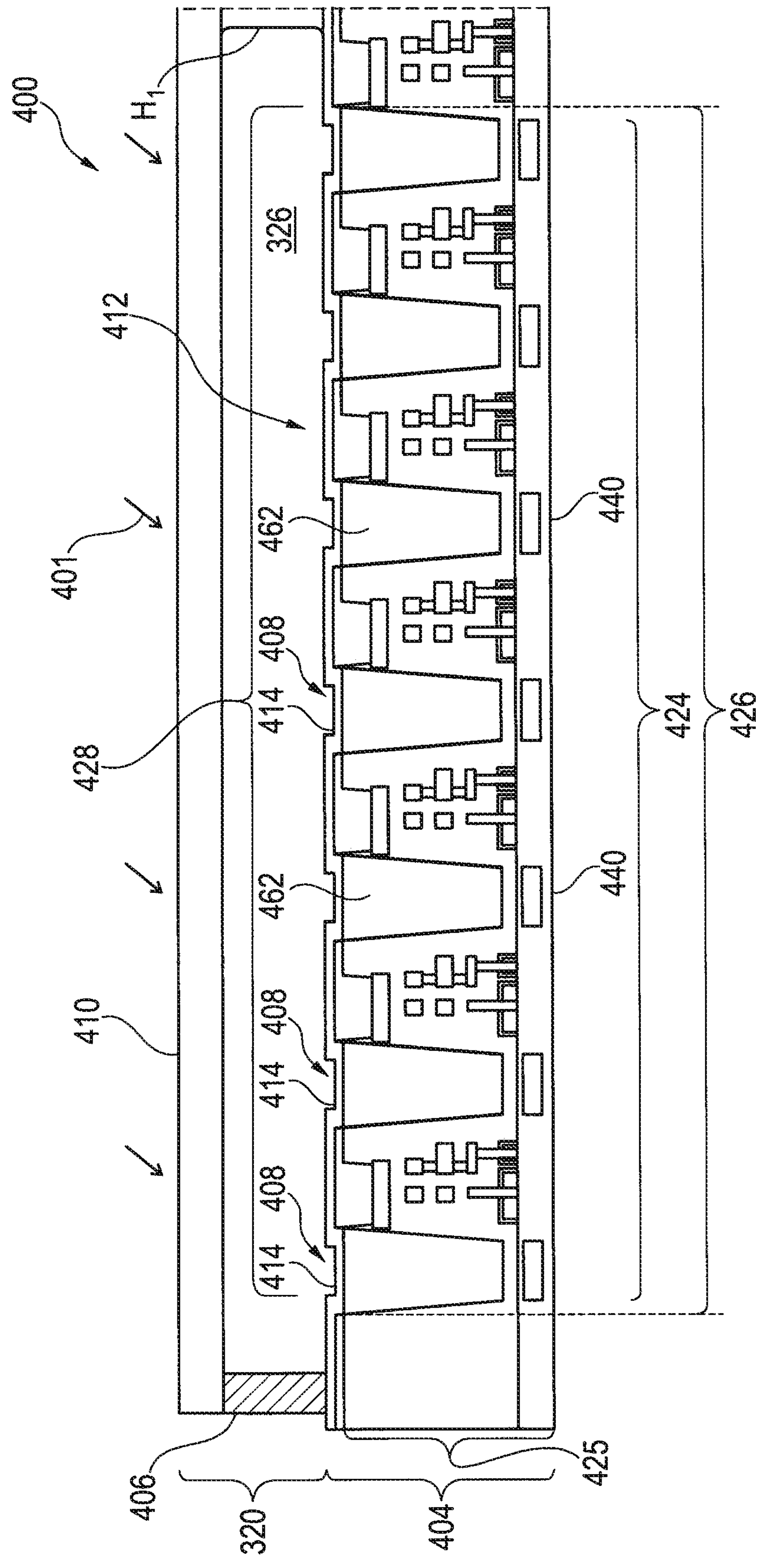
FIG. 11 is a cross-section of a detection assembly that may be used to detect designated reactions from a reaction chamber.

At stage 9, the pump assembly 332 draws the combined biological samples/hydrogenation buffer through the reservoir port 222E, through the flow channel 218, through the feed port 226, and into the reaction chamber 326 (FIG. 2). The biological samples may be immobilized to surfaces that define the reaction chamber. For example, clusters may be formed that include the biological samples. Stages 10-13 represent a sequencing cycle. At stage 10, the rotary valve 216 may be at a third valve position so that a nucleotides solution may be drawn through the flow channel 218 and into the reaction chamber. At such time, a nucleotide may be incorporated into the corresponding biological samples (e.g., primers annealed to template nucleic acids). At stage 11, the rotary valve 216 may be at a fourth valve position so that a wash solution may flow through the reaction chamber and carry the nucleotides solution away from the reaction chamber. After stage 11, the reaction chamber may be imaged by the imaging detector, such as the detection device 404 (FIG. 11). The color of light emitted from the clusters may be used to identify the bases incorporated by the clusters. At stage 12, the rotary valve 216 may be at a fourth valve position so that a cleaving solution may flow through the reaction chamber and the fluorophores (and, if present, reversible terminator moieties) may be removed from the clusters. At stage 13, the rotary valve 216 may be at the third valve position again and the wash solution may flow through the reaction chamber to remove the cleaving solution. Stages 10-13 may be repeated until completion of the sequencing and/or until reagents are depleted.

TABLE 1

| | Port | Type of Fluid Flowing into Flow Channel | Flow Direction |
|---|---|---|---|
| Stage 1 | 210 | 1st Biological Sample | Toward feed port 226 |
| Stage 2 | 222E | 1st Biological Sample | Away from feed port 226 |
| Stage 3 | 210 | 2nd Biological Sample | Toward feed port 226 |
| Stage 4 | 222E | 2nd Biological Sample | Away from feed port 226 |
| Stage 5 | 210 | 3rd Biological Sample | Toward feed port 226 |
| Stage 6 | 222E | 3rd Biological Sample | Away from feed port 226 |
| Stage 7 | 210 | 4th Biological Sample | Toward feed port 226 |
| Stage 8 | 222E | 4th Biological Sample | Away from feed port 226 |
| Stage 9 | 222E | Combined Biological Samples + Hydrogenation Buffer | Toward feed port 226 |
| Stage 10 | 222A | Nucleotides Solution | Toward feed port 226 |
| Stage 11 | 222B | Wash Solution | Toward feed port 226 |
| Stage 12 | 222C | Cleaving Solution | Toward feed port 226 |
| Stage 13 | 222B | Wash Solution | Toward feed port 226 |
| Repeat Stages 10-13 until detection complete | | | |

FIG. 11 illustrates a cross-section of a portion of a detection assembly 400. In the illustrated embodiment, the detection assembly 400 is integrally formed with the flow cell 320. More specifically, the detection assembly includes a detection device 404, which is positioned adjacent to the flow cell 320 and the reaction chamber 326. The flow cell 320 may be mounted to the detection device 404. In the illustrated embodiment, the flow cell 320 is affixed directly to the detection device 404 through one or more securing mechanisms (e.g., adhesive, bond, fasteners, and the like). In some embodiments, the flow cell 320 may be removably coupled to the detection device 404. In particular embodiments, the detection device 404 is configured to detect light signals from the reaction chamber 326. Accordingly, the detection device 404 may be referred to as an imaging detector in some embodiments.

In the illustrated embodiment, the detection device 404 includes a device base 425. In particular embodiments, the device base 425 includes a plurality of stacked layers (e.g., silicon layer, dielectric layer, metal-dielectric layers, etc.). The device base 425 may include a sensor array 424 of light sensors 440, a guide array 426 of light guides 462, and a reaction array 428 of reaction recesses 408 that have corresponding reaction sites 414. In certain embodiments, the components are arranged such that each light sensor 440 aligns with a single light guide 462 and a single reaction site 414. However, in other embodiments, a single light sensor 440 may receive photons through more than one light guide 462 and/or from more than one reaction site 414. As used herein, a single light sensor may include one pixel or more than one pixel. The detection device 404 may be manufactured using complementary-metal-oxide semiconductor (CMOS) technology. In particular embodiments, the detection device 404 is a CMOS imaging detector.

It is noted that the term “array” or “sub-array” does not necessarily include each and every item of a certain type that the detection device may have. For example, the sensor array 424 may not include each and every light sensor in the detection device 404. Instead, the detection device 404 may include other light sensors (e.g., other array(s) of light sensors). As another example, the guide array 426 may not include each and every light guide of the detection device. Instead, there may be other light guides that are configured differently than the light guides 462 or that have different relationships with other elements of the detection device 404. As such, unless explicitly recited otherwise, the term “array” may or may not include all such items of the detection device.

In the illustrated embodiment, the flow cell 320 includes a sidewall 406 and a flow cover 410 that is supported by the sidewall 406 and other sidewalls (not shown). The sidewalls are coupled to the detector surface 412 and extend between the flow cover 410 and the detector surface 412. In some embodiments, the sidewalls are formed from a curable adhesive layer that bonds the flow cover 410 to the detection device 404.

The flow cell 320 is sized and shaped so that the reaction chamber 326 exists between the flow cover 410 and the detection device 404. As shown, the reaction chamber 326 may include a height $H_1$. By way of example only, the height $H_1$ may be between about 50-400 μm (microns) or, more particularly, about 80-200 μm. In the illustrated embodiment, the height $H_1$ is about 100 μm. The flow cover 410 may include a material that is transparent to excitation light 401 propagating from an exterior of the detection assembly 400 into the reaction chamber 326. As shown in FIG. 7, the excitation light 401 approaches the flow cover 410 at a non-orthogonal angle. However, this is only for illustrative purposes as the excitation light 401 may approach the flow cover 410 from different angles. The reaction chamber 326 is sized and shaped to direct a fluid along the detector surface 412. The height $H_1$ and other dimensions of the reaction chamber 326 may be configured to maintain a substantially even flow of a fluid along the detector surface 412. The dimensions of the reaction chamber 326 may also be configured to control bubble formation.

The sidewalls 406 and the flow cover 410 may be separate components that are coupled to each other. In other embodiments, the sidewalls 406 and the flow cover 410 may be integrally formed such that the sidewalls 406 and the flow cover 410 are formed from a continuous piece of material. By way of example, the flow cover 410 (or the flow cell 320) may comprise a transparent material, such as glass or plastic. The flow cover 410 may constitute a substantially rectangular block having a planar exterior surface and a planar inner surface that defines the reaction chamber 326. The block may be mounted onto the sidewalls 406. Alternatively, the flow cell 320 may be etched to define the flow cover 410 and the sidewalls 406. For example, a recess may be etched into the transparent material. When the etched material is mounted to the detection device 404, the recess may become the reaction chamber 326.

The detection device 404 has a detector surface 412 that may be functionalized (e.g., chemically or physically modified in a suitable manner for conducting designated reactions). For example, the detector surface 412 may be functionalized and may include a plurality of reaction sites 414 having one or more biomolecules immobilized thereto. The detector surface 412 has an array of reaction recesses or open-sided reaction recesses 408. Each of the reaction recesses 408 may include one or more of the reaction sites

414. The reaction recesses 408 may be defined by, for example, an indent or change in depth along the detector surface 412. In other embodiments, the detector surface 412 may be substantially planar.

As shown in FIG. 11, the reaction sites 414 may be distributed in a pattern along the detector surface 412. For instance, the reactions sites 414 may be located in rows and columns along the detector surface 412 in a manner that is similar to a microarray. However, it is understood that various patterns of reaction sites may be used. The reaction sites may include biological or chemical substances that emit light signals. For example, the biological or chemical substances of the reactions sites may generate light emissions in response to the excitation light 401. In particular embodiments, the reaction sites 414 include clusters or colonies of biomolecules (e.g., nucleic acids) that are immobilized on the detector surface 412.

Figure 12:
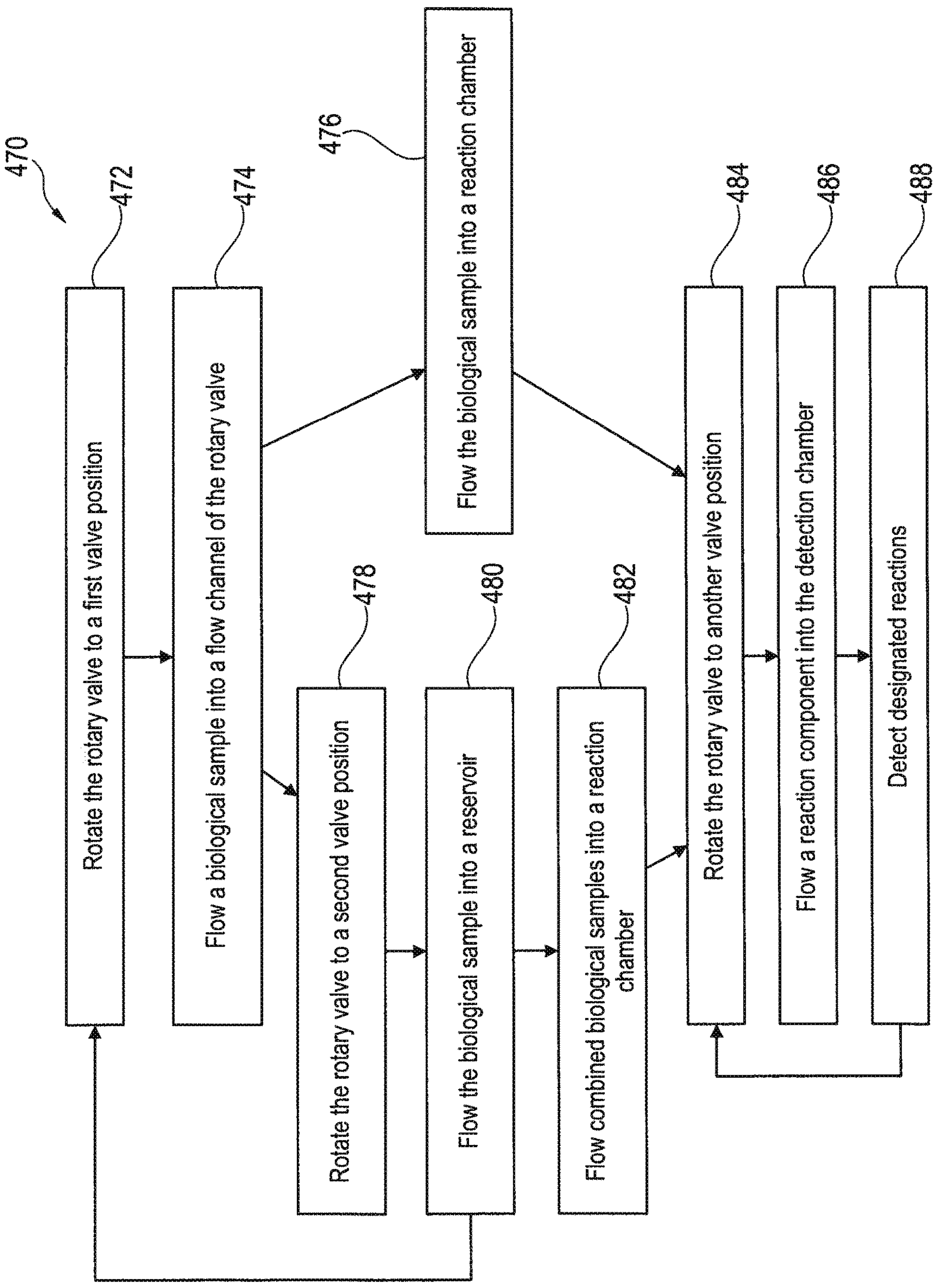
FIG. 12 is a flowchart of a method in accordance with an embodiment.

FIG. 12 is a flowchart of a method 470. In some embodiments, the method 470 may include preparing a biological sample and/or detecting designated reactions of the biological sample for analysis. The method 470 may, for example, employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 470 may be performed or executed using a flow-control system that is similar or identical to the flow-control system 200 (FIG. 2). The method 470 includes rotating (at 472) a rotary valve to a first valve position. The rotary valve has at least one flow channel. In the first valve position, the flow channel may be in flow communication with a sample channel (or other reservoir of the flow-control system) and in flow communication with a reaction chamber such that the flow channel fluidically couples the sample channel and the reaction chamber. For example, the rotary valve may have first and second channel ports. The first channel port may be aligned with a port (e.g., a supply port or reservoir port) and the second channel port may be aligned with a feed port. When the rotary valve is in the first valve position, other ports may be sealed by the rotary valve such that fluid is blocked from flowing through the other ports.

The method 470 may also include flowing (at 474) a biological sample from a sample channel (or a first reservoir) into the flow channel when the rotary valve is in the first valve position. For example, the biological sample may flow through a supply port into the flow channel of the rotary valve. As another example, the biological sample may be disposed within a reservoir, such as a reservoir that contains hydrogenation buffer. The biological sample (with hydrogenation buffer) may flow through a reservoir port and into the flow channel.

Optionally, the biological sample may continue to flow (at 476) into the reaction chamber. Alternatively, the method 470 may include rotating (at 478) the rotary valve to a second valve position while the biological sample is disposed within the flow channel. In the second valve position, the flow channel may be fluidically coupled to another reservoir, such as a reservoir that contains a hydrogenation buffer. At 480, the biological sample within the flow channel may be induced to flow (e.g., by a pump assembly) into the reservoir. The method 470 may then include repeating steps 472, 474, 478, and 480 until each of the desired biological samples is disposed within a common reservoir. At 482, the biological samples with the hydrogenation buffer may simultaneously flow through the flow channel and into the reaction chamber.

Accordingly, one or more biological samples may be directed into the reaction chamber utilizing the rotary valve. In alternative embodiments, the biological sample (or samples) has a direct channel to the reaction chamber and does not flow through the rotary valve. Optionally, the method 470 may begin cycling through designated operations to conduct the designated reactions, such as the operations described with respect to Table 1. For example, the rotary valve may be rotated (at 484) to another valve position to fluidically couple the reaction chamber to a designated reservoir. At 486, a reaction component may flow into the reaction chamber to interact with the biological sample(s) therein. Optionally, at 488, the method 470 includes detecting the designated reactions within the reaction chamber. The method 470 may then return to step 484.

Figure 13:
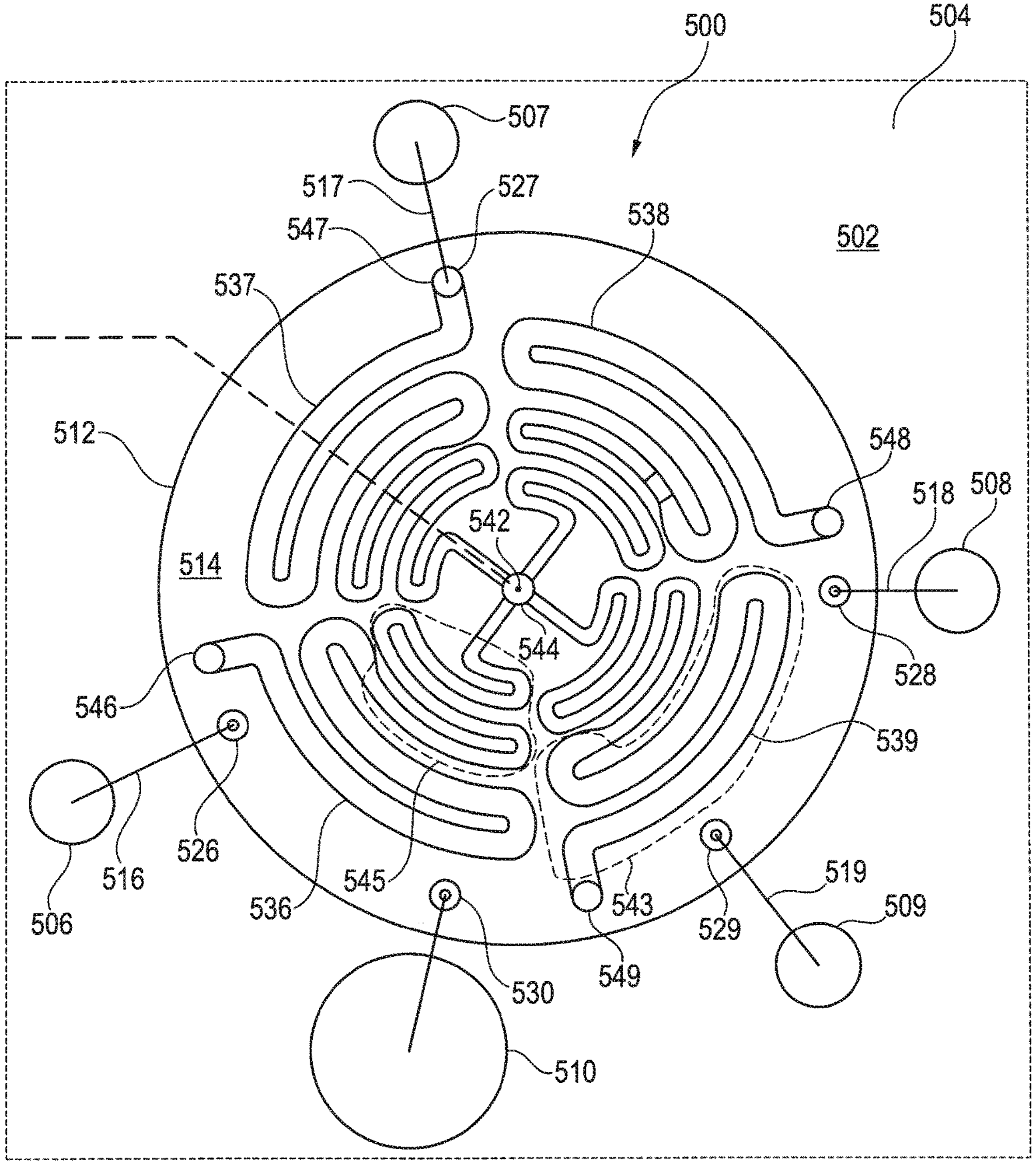
FIG. 13 is a plan view of a rotary valve formed in accordance with an embodiment that is rotatably mounted to a microfluidic body.

FIG. 13 is a plan view of a rotary valve 500 formed in accordance with an embodiment that is rotatably mounted to a body side 502 of a microfluidic body 504. The rotary valve 500 may include similar features as the rotary valve 216 (FIG. 2). The microfluidic body 504 includes a plurality of reservoirs 506-510 that are configured to hold reaction components and/or biological samples. More specifically, the reservoirs 506-509 hold first, second, third, and fourth biological samples (or sample liquids). The reservoir 510 includes a hydrogenation buffer. Each of the reservoirs 506-510 is fluidically coupled to a corresponding port through a respective reservoir channel 516-520, which are represented by lines in FIG. 13. As shown, the ports include reservoir or supply ports 526-530 that open to the body side 502 and are in flow communication with the reservoirs 506-510. The microfluidic body 504 also includes a feed port 524 (shown in FIG. 13) that opens to the body side 502.

The rotary valve 500 includes a valve body 512 having a fluidic side 513 (shown in FIG. 14) that engages the body side 502 and an opposite operative side 514. The valve body 512 includes first, second, third, and fourth flow channels 536-539. Each of the flow channels 536-539 is configured to hold a biological sample during an amplification or PCR protocol. Each of the flow channels 536-539 has a common channel port (or outlet port) 544 that is centrally located. In other embodiments, the flow channels 536-539 do not share the same channel port. The common channel port 544 is located at an axis 542 about which the rotary valve 500 rotates. The flow channels 536-539 include respective first channel ports (or inlet ports) 546-549. Accordingly, each of the flow channels 536-539 extends from a respective first channel port 546-549 to a common channel port 544. Similar to the rotary valve 216 (FIG. 2), the rotary valve 500 is configured to rotate to different valve positions to fluidically couple reservoirs and channels. Unlike the rotary valve 500, however, the rotary valve 500 may be used during an amplification protocol. More specifically, the valve body 512 may engage a thermocycler 570 (shown in FIG. 14) while the biological samples are held within the flow channels 536-539.

In some embodiments, the flow channels 536-539 may have anti-diffusion segments 545. The anti-diffusion segments 545 are configured to reduce the likelihood of diffusion occurring as the biological sample within the flow channels 536-539 is subjected to a PCR protocol. For example, the flow channels 536-539 shown in FIG. 13 have non-linear paths and dimensions that change along the path.

More specifically, the flow channels 536-539 having serpentine or wavy paths that wrap back and forth as the flow channel extends from the corresponding first channel port toward the common channel port 544. The first channel ports 546-549 have radially outward locations. In addition to the shape of the flow channels 536-539, the flow channels 536-539 have dimensions that reduce as the flow channel 536-539 extends from the corresponding first channel port to the common channel port 544. In other embodiments, the anti-diffusion segments 545 do not have a serpentine path. Segments of the flow channels 536-539 that do not include the anti-diffusion segment 545 may be referred to as the sample-preparation region 543 that represents a portion of the corresponding flow channel where the biological sample may experience different conditions, such as temperature changes. It should be understood, however, that the biological sample may also exist within the anti-diffusion segments 545 for at least some embodiments.

Figure 14:
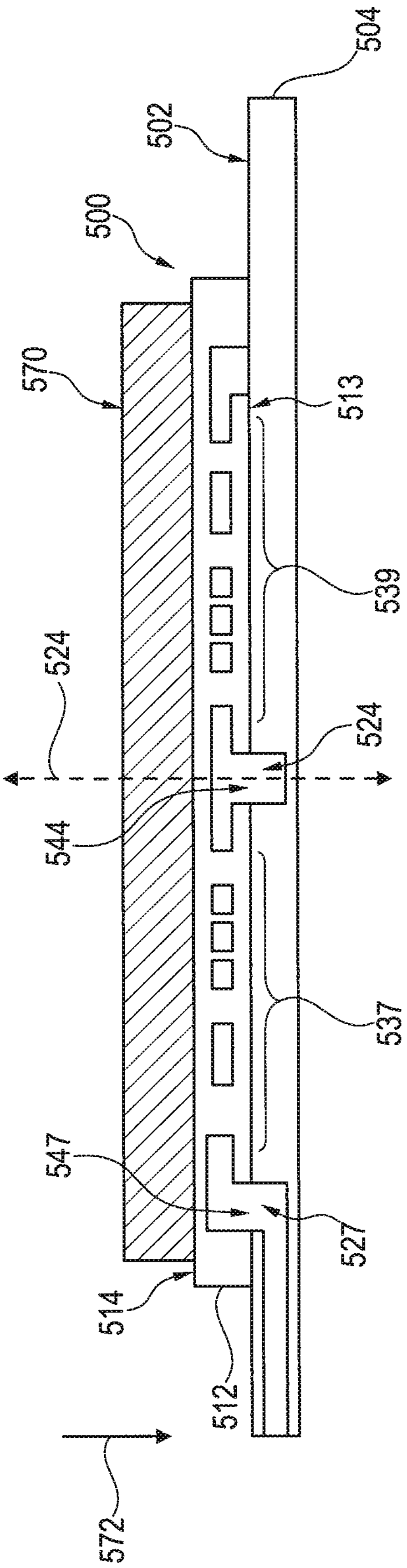
FIG. 14 is a cross-section of the rotary valve of FIG. 13 that is rotatably mounted to the microfluidic body.

FIG. 14 illustrates a side cross-section of the rotary valve 500 when the thermocycler 570 is mounted to the operative side 514. In some embodiments, the thermocycler 570 may provide a mounting force 572 that presses the valve body 512 against the body side 502 of the microfluidic body 504. Although not shown in FIG. 14, the valve body 512 may include one or more mechanical interfaces (e.g., non-planar features, such as fins) that are engaged by the thermocycler 570. The thermocycler 570 is configured to control a temperature of the flow channels 536-539. In particular embodiments, the thermocycler 570 simultaneously controls the temperature of each of the flow channels 536-539. In other embodiments, the thermocycler 570 may selectively engage less than all of the flow channels at a single time.

As shown in FIG. 14, the common channel port 544 is fluidically coupled to the feed port 524. The axis 542 extends through the common channel port 544 and the feed port 524. The first channel port 547 of the flow channel 537 is fluidically coupled to a reservoir port 527. However, the first channel port 549 of the flow channel 539 is sealed by the body side 502. Accordingly, in the valve position shown in FIG. 14, fluid (e.g., fluid containing the biological sample) may flow from the reservoir 507 (FIG. 13) and into the flow channel 537.

Figures 15A, 15B, 15C, 15D, 15E, 15F:
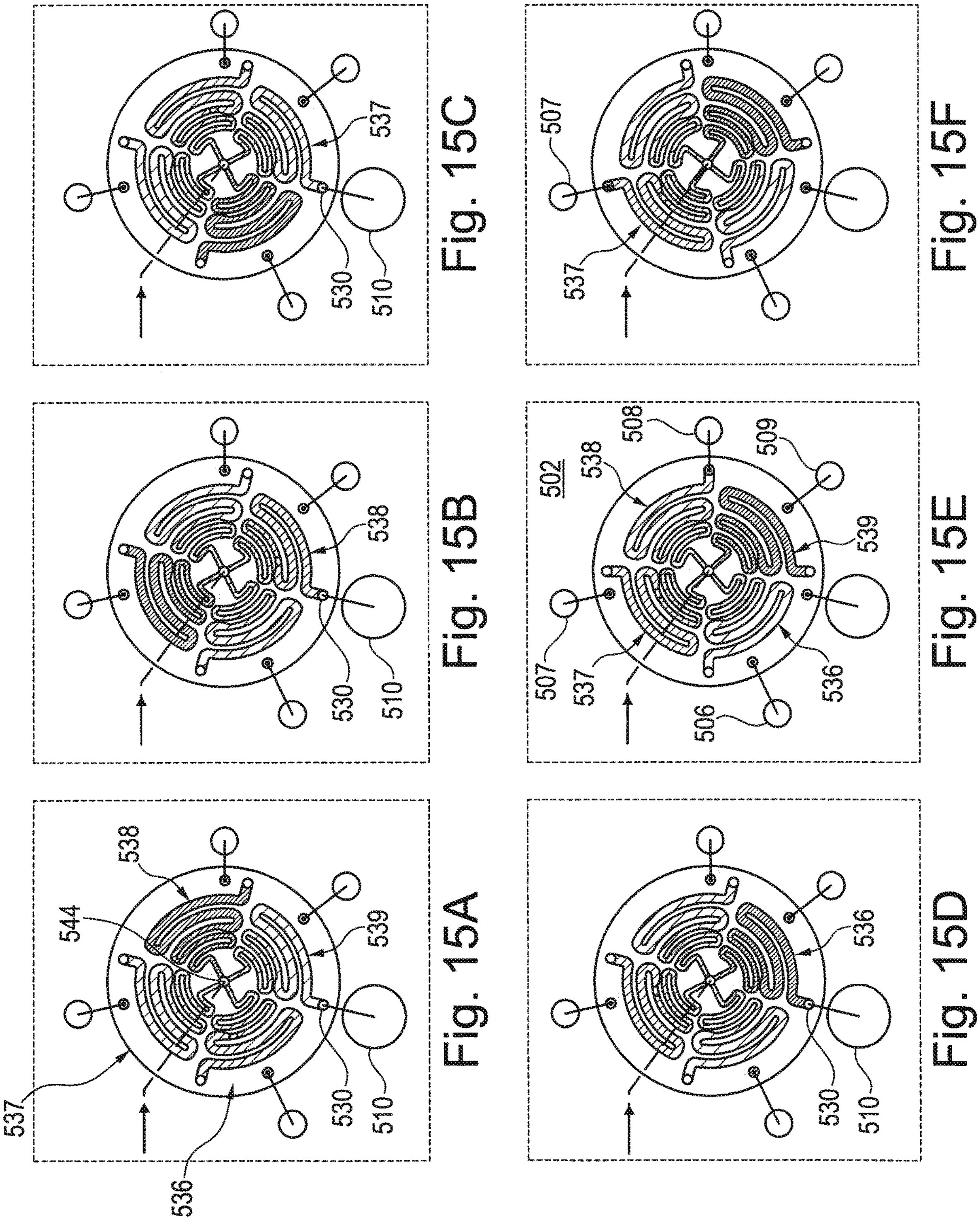
FIGS. 15A-15L illustrate different rotational positions of the rotary valve during different stages of an assay protocol.

FIGS. 15A-15L are plan views of the rotary valve 500 and illustrate different valve positions where different operations may occur. To prepare for the amplification protocol, a system controller, such as the system controller 180 (FIG. 1), is configured to selectively control a pump assembly (not shown) and the rotary valve 500. The pump assembly may be similar to the pump assembly 332 and include one or more flow pumps. In some embodiments, a single pump may be downstream with respect to the rotary valve 500 and be configured to pull fluids through the common channel port 544 (FIG. 15A).

Optionally, the flow channels 536-539 (FIG. 15A) may be primed with a fluid prior to receiving the biological sample. For example, FIGS. 15A-15D show the first channel port of a corresponding flow channel fluidically coupled to the reservoir port 530, which is in flow communication with the reservoir 510. Accordingly, the first channel port of each flow channel may be individually coupled to the reservoir 510. When the flow channel is in flow communication with the reservoir 510, the system controller may selectively activate the pump assembly to induce flow of the reaction component within the reservoir 510 so that the reaction component flows into the corresponding flow channel.

Accordingly, after FIG. 15D, each of the flow channels 536-539 is primed with a reaction component. Although the reaction component is associated with the reservoir 510, other reaction components may be used to prime the flow channels 536-539. For example, the flow channels 536-539 may fluidically couple to a separate reservoir (not shown) that contains, for example, water or a buffer solution. In the illustrated embodiment, each of the flow channels 536-539 separately couples to the reservoir 510. In alternative embodiments, one or more of the flow channels 536-539 may simultaneously couple to the reservoir 510 or to separate reservoirs.

Figure 15G:
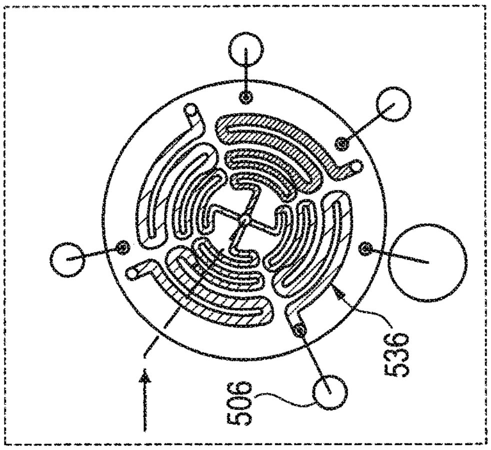
Figure 15H:
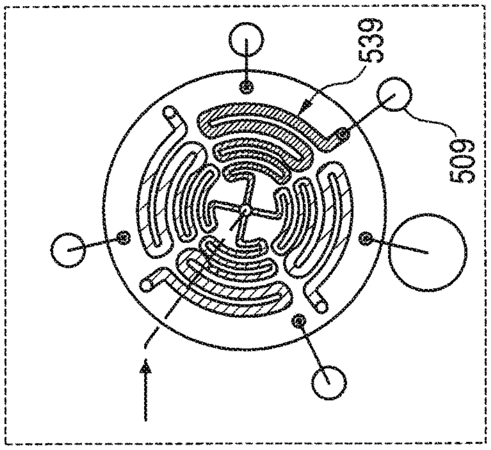
Figure 15I:
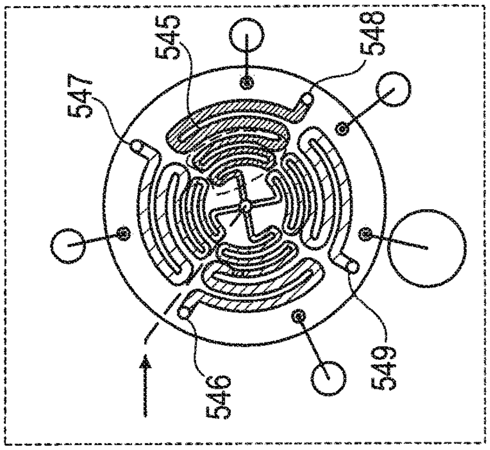

After the flow channels 536-539 have been primed, the biological sample from the reservoirs 506-509 (FIG. 15E) may be loaded into the flow channels 536-539 (FIG. 15E), respectively. For example, as shown in FIG. 15E, the flow channel 538 is fluidically coupled to the reservoir port 528 and, as such, in flow communication with the reservoir 508. At this time, the flow channels 536, 537, and 539 are covered by the body side 502. The pump assembly may induce a flow of the biological sample within the reservoir 508 so that the biological sample flows into the flow channel 538. The amount of flow may be based on the amount of fluid within the reservoir 508. After the biological sample has been loaded into the flow channel 538, the rotary valve 500 may be selectively rotated and the pump assembly, in a similar manner, may be selectively activated to load the biological samples that are the reservoirs 506, 507, and 509 into the flow channels 536, 537, and 539, respectively, as shown in FIGS. 15F-15H.

With the biological samples loaded within the respective flow channels 536-539, the rotary valve 500 may be selectively rotated such that each of the first channel ports 546-549 is covered (or sealed) by the body side 502 of the microfluidic body 504. The valve position in which the first channel ports 546-549 are sealed is shown in FIG. 151. The thermocycler 570 (FIG. 14) may then be controlled to cycle through temperature changes in accordance with a designated amplification protocol. Although the flow channels 536-539 are only sealed at one end, the pump assembly and the anti-diffusion segments 545 may resist movement and/or diffusion of the biological sample (e.g., PCR plug) into or through the feed port 524 (FIG. 14).

Figure 15J:
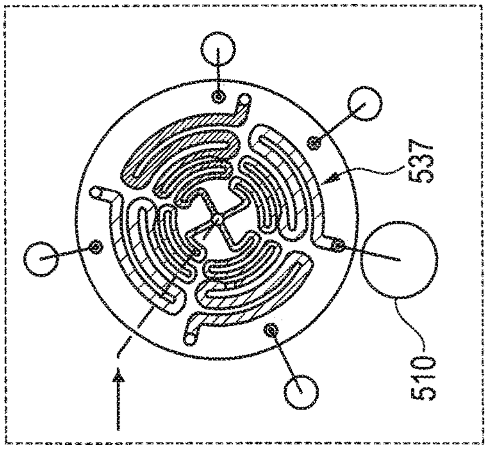
Figure 15K:
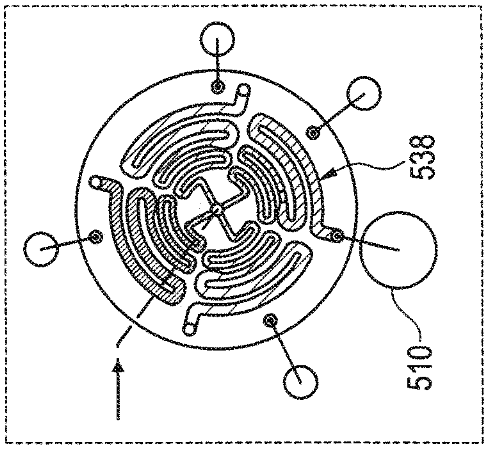
Figure 15L:
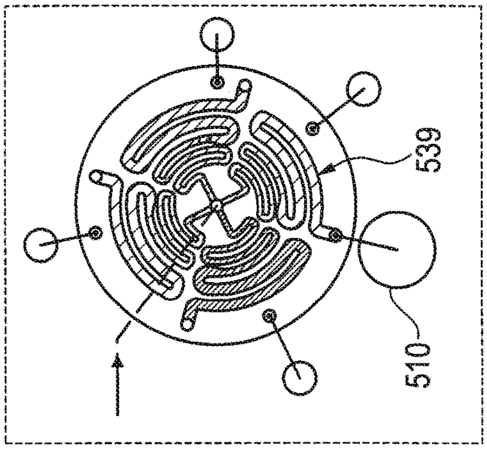

After the amplification protocol, the biological samples may be loaded into a common reservoir. For instance, as shown in FIGS. 15J-15L, the biological samples within the flow channels 536-538 may be fluidically coupled to the reservoir 510. The pump assembly may be selectively operated to induce flow of the biological sample into the reservoir 510. Although not shown, the flow channel 536 may also be fluidically coupled to the reservoir 510 so that the biological sample within the flow channel 536 may be loaded into the reservoir 510. Accordingly, each of the biological samples from the reservoir 506-509 may be loaded into a common reservoir 510 after the amplification protocol. The pump assembly may then be selectively activated to induce flow of the mixed biological samples through the feed port 524. The biological samples may be fluidically delivered to a reaction chamber, such as the reaction chamber 326 (FIG. 2). The biological samples may then undergo designated reactions as described herein. In particular embodiments, the biological samples may be used during an SBS protocol.

Figure 16:
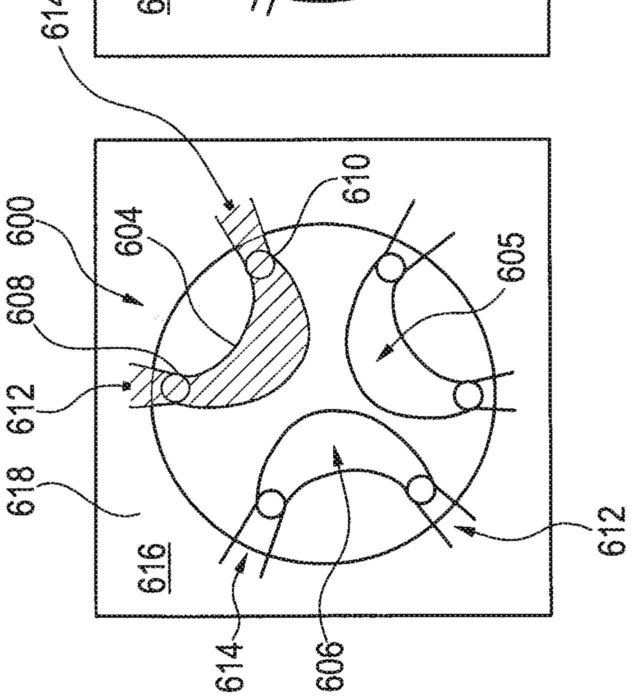
FIG. 16 is a plan view of a rotary valve formed in accordance with an embodiment.

FIG. 16 is a plan view of a rotary valve 600 formed in accordance with an embodiment that is mounted to a body side 616 of a microfluidic body 618. The rotary valve 600 may include similar features as the rotary valve 216 (FIG. 2) and the rotary valve 500 (FIG. 13). The rotary valve 600 includes a valve body 602 having flow channels 604-606.

Each of the flow channels 604-606 extends between a first channel port (or inlet port) 608 and a second channel port (or outlet port) 610. Unlike the rotary valve 500, the flow channels 604-606 are not in flow communication with a common channel port.

In the illustrated embodiment, each of the flow channels 604-606 is in flow communication with an upstream channel 612 and a downstream channel 614. In FIG. 16, the rotary valve 600 is in a valve position such that each of the flow channels 604-606 may receive a biological sample from the corresponding upstream channel 612. For instance, the flow channels 604-606 may simultaneously receive the corresponding biological sample. The flow of the biological samples into the flow channels 604-606 may be induced by a common pump. For example, the downstream channels 614 may merge together and fluidically coupled to a single pump. Alternatively, separate pumps may be fluidically coupled to the flow channels 604-606.

Figure 17:
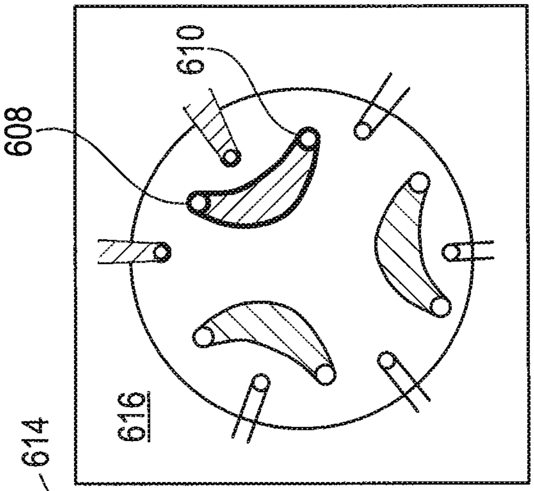
FIG. 17 is a plan view of the rotary valve of FIG. 16 during an amplification protocol.

FIG. 17 is a plan view of the rotary valve 600 after the rotary valve has been rotated to a valve position in which the first and second channel ports 608, 610 for each of the flow channels 604-606 is sealed by the body side 616 of the microfluidic body 618. In the valve position shown in FIG. 17, a thermocycler (not shown) may engage the valve body 602 to control a temperature experienced within the flow channels 604-606. As such, the biological samples may undergo an amplification protocol as described herein. Unlike the embodiment shown in FIGS. 13-15, the flow channels 604-606 are sealed at both ends to reduce the likelihood of diffusion and movement of the PCR plug.

Figure 18:
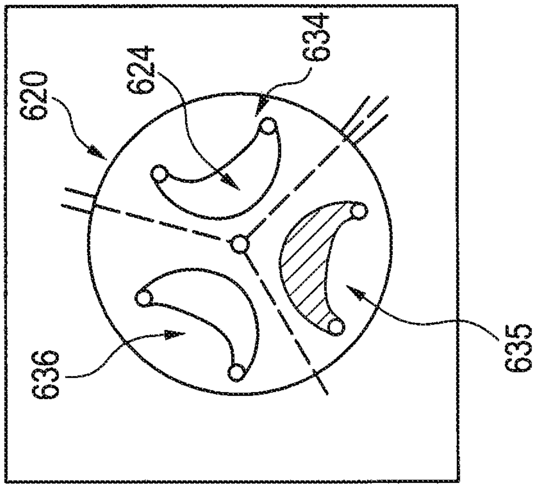
FIG. 18 is a plan view of a rotary valve formed in accordance with an embodiment.

FIG. 18 is a plan view of a rotary valve 620 formed in accordance with an embodiment. The rotary valve 620 may be similar or identical to the rotary valve 600 (FIG. 16) and include a plurality of flow channels 624-626. As shown, the rotary valve 600 is separated into three thermal-control areas or zones 634-636. The thermal-control areas 634-636 are represented by pie-shaped areas that are indicated by dashed lines. Each thermal-control area 634-636 represents a different temperature range controlled by one or more thermocyclers (not shown). More specifically, after the biological samples are loaded into the flow channels 624-626, the rotary valve 620 may be selectively rotated to different positions. The flow channel within the thermal-control area 634 may experience a designated temperature for denaturing nucleic acids. The flow channel within the thermal-control area 635 may experience a designated temperature for an annealing-extension stage, and the flow channel within the thermal-control area 636 may experience a designated temperature for a pre-heating and/or temperature holding stage. The system controller may selectively rotate the rotary valve 620 to three different valve positions to cycle the biological samples through multiple PCR amplification stages. Thus, unlike the flow channels of the rotary valve 600, the flow channels 624-626 experience different temperatures.

Figure 19:
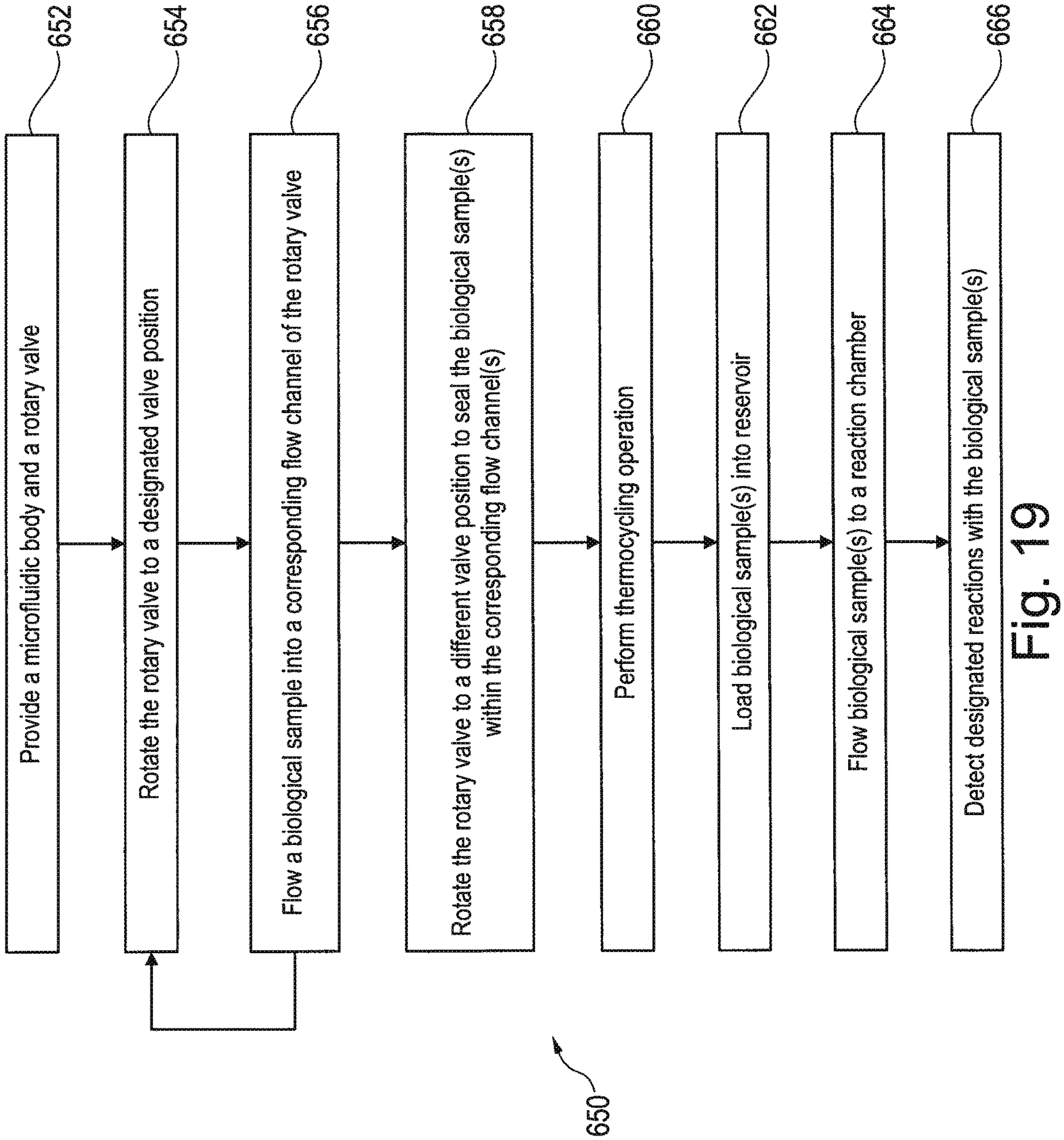
FIG. 19 is a method in accordance with an embodiment.

FIG. 19 is a flowchart illustrating a method 650. In some embodiments, the method 650 may include preparing a biological sample and, optionally, detecting designated reactions of the biological sample for analysis. The method 650 may, for example, employ structures or aspects of various embodiments (e.g., systems and/or methods) described herein, such as the embodiments described with respect to FIGS. 13-18. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 650 may include providing (at 652) a microfluidic body and a rotary valve. The microfluidic body may have a body side and a fluidic network that includes a supply port, such as the reservoir ports 526-529, and a feed port. The supply port may open to the body side. The rotary valve may be rotatably mounted to the body side and have a first channel port, a second channel port, and a flow channel that extends between the first channel port and the second channel port. In some embodiments, multiple flow channels may be used in which the flow channels have separate second channel ports, such as the embodiments of FIGS. 16-18, or share the second channel port, such as the embodiment of FIGS. 13-15. In such embodiments in which the second channel port is shared, the second channel port may be referred to as a common channel port.

The method 650 may include rotating (at 654) the rotary valve to a first valve position at which the first channel port is in flow communication with the supply port of the microfluidic body. The method 650 may also include flowing (at 656) a biological sample through the first channel port and into the flow channel when the rotary valve is in the first valve position. The biological sample may flow in a direction that is from the first channel port and toward the second channel port. The flowing (at 656) may include selectively controlling the flow rate and/or duration of the flowing such that the biological sample does not substantially flow past the second channel port or the feed port. For embodiments that include multiple flow channels, such as the rotary valve 500, the steps 654 and 656 may be repeated until each of the flow channels has a corresponding biological sample therein. However, the rotating (at 654) for each flow channel is not to the same valve position. More specifically, when the biological sample is flowed into a corresponding flow channel, the other flow channels may be sealed at one end or both ends.

The method 650 may also include rotating (at 658) the rotary valve to a second valve position with the biological sample within the flow channel such that the first channel port is sealed by the body side and performing (at 660) a thermocycling operation to change a temperature of the biological sample in the flow channel to a select temperature. The performing (at 660) may be in accordance with a predetermined schedule. For example, the schedule may be to execute a PCR operation in order to amplify the biological sample for subsequent analysis.

Optionally, after the performing (at 660), the biological sample or biological samples may be loaded (at 662) into a reservoir. For example, the reservoir may include hydrogenation buffer solution that prepares the biological sample for subsequent analysis. At 664, the biological sample (or the combined biological samples) may be delivered to a reaction chamber for subsequent analysis at 666.

Figure 20:
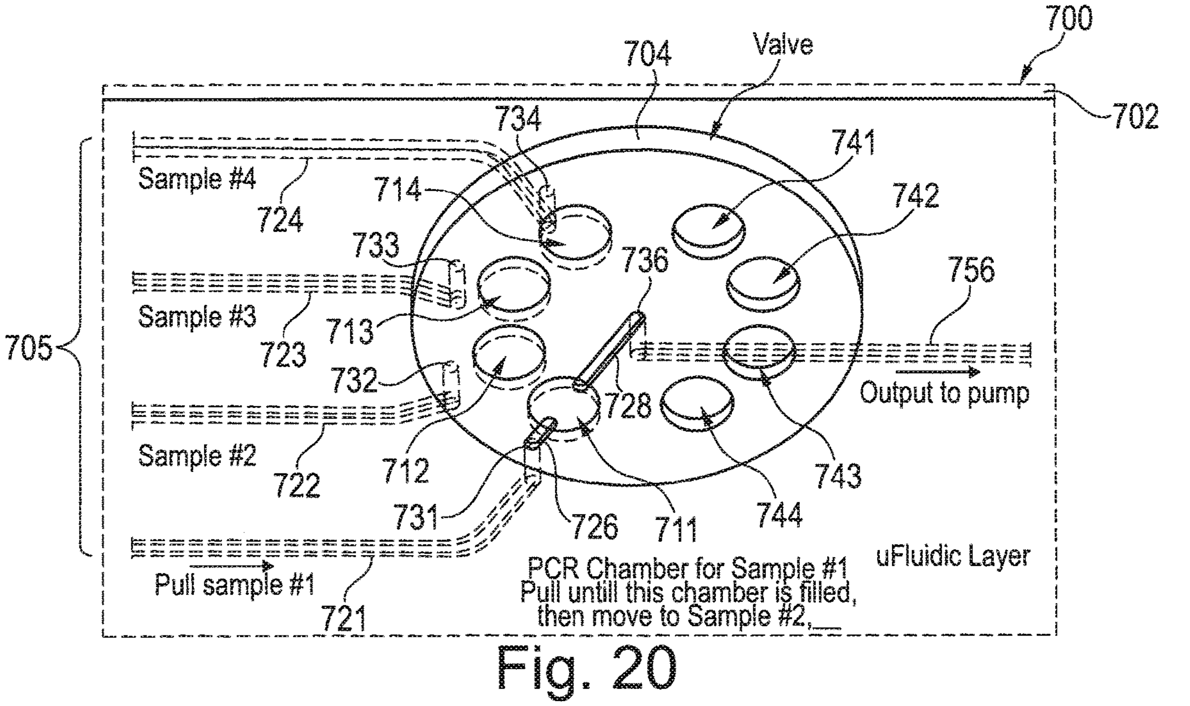
FIG. 20 is a perspective view of a flow-control system formed in accordance with an embodiment that includes a rotary valve and a microfluidic body.
Figure 22:
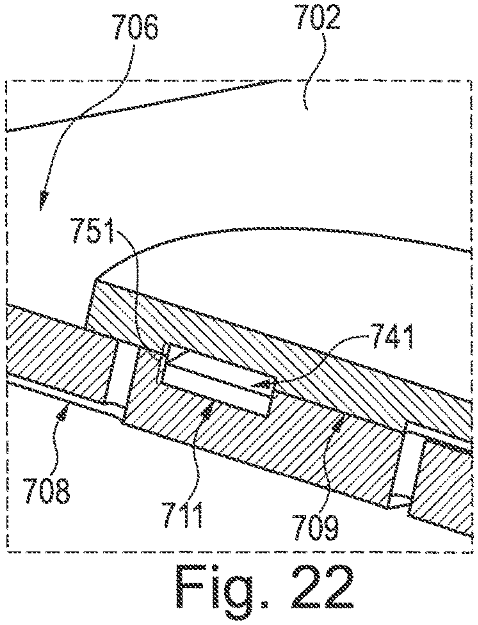
FIG. 22 is an isolated cross-section of the flow-control system of FIG. 20.

FIG. 20 is a perspective view of flow-control system 700 formed in accordance with an embodiment that includes a microfluidic body 702 and a rotary valve 704. Unlike the rotary valves 500 (FIG. 13), 600 (FIG. 16), and 620 (FIG. 18), amplification does not occur solely within the rotary valve 704. Instead, amplification occurs at least partially within the microfluidic body 702. More specifically, the microfluidic body 702 has a first body side 706 (shown in FIG. 22) and a second body side 708 (shown in FIG. 22) that face in opposite directions. The microfluidic body 702 has a fluidic network 705 that includes a plurality of sample reservoirs 711-714, a plurality of supply channels 721-724 with corresponding inlet ports 731-734, and a common outlet port 736. The inlet ports 731-734 and the outlet port 736 open to the first body side 706 (FIG. 22).

The rotary valve 704 is rotatably mounted to the microfluidic body 702 along first body side 706. In the illustrated embodiment, the rotary valve 704 has a first channel segment 726 and a second channel segment 728. The first and second channel segments 726, 728 may open to a fluidic side 709 (shown in FIG. 22) of the rotary valve 704. Alternatively, the first and second channel segments 726, 728 may extend between corresponding channel ports that open to the fluidic side 709. The first and second channel segments 726, 728 are separate from each other and extend along only a portion of the fluidic side 709. In an exemplary embodiment, the second channel segment 728 is in flow communication with the outlet port 736 at any rotational position of the rotary valve 704.

FIG. 20 shows the rotary valve 704 in a designated position in which the sample reservoir 711 is in flow communication with a pump assembly. More specifically, the first channel segment 726 is fluidically interposed between the inlet port 731 and the sample reservoir 711. The second channel segment 726 is fluidically interposed between the sample reservoir 711 and the outlet port 736. As such, the supply channel 721 is in flow communication with a feed channel 756 through the first channel segment 726, the sample reservoir 711, and the second channel segment 728.

Although not shown, the flow-control system 700 may include a pump assembly that is configured to induce a flow of fluid through the inlet port 731 and the first channel segment 726 into the sample reservoir 711. The fluid may include a biological sample that is loaded within, for example, a remote reservoir (not shown) that is in flow communication with the supply channel 721. The flowing of the fluid and the dimensions of the sample reservoir may be configured such that the biological sample does not substantially exit the sample reservoir 711 through the second channel segment 728. After the biological sample is loaded into the sample reservoir 711, the rotary valve 704 may be selectively rotated such that the first channel segment 726 and the second channel segment 728 fluidically couple to the sample reservoir 712. The sample reservoir 712 may be loaded with a biological sample that flows from the supply channel 722. In a similar manner, the sample reservoirs 713 and 714 may be loaded with a corresponding biological sample.

Figure 21:
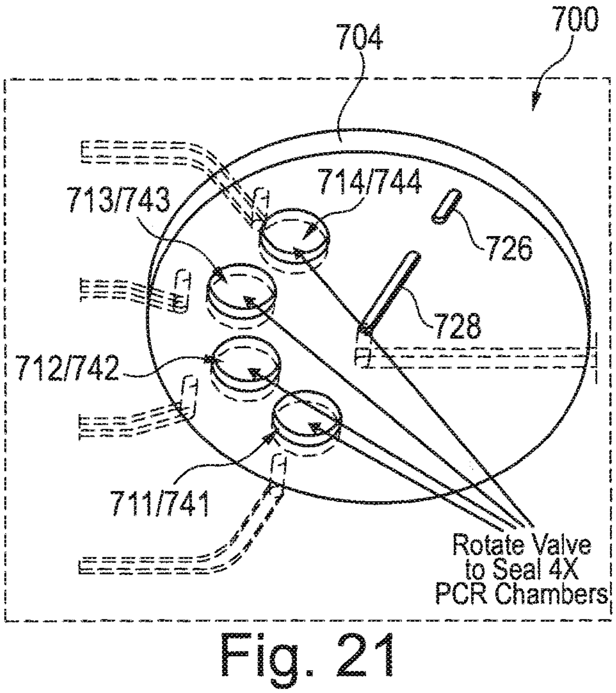
FIG. 21 is a perspective view of the flow-control system of FIG. 20 when the rotary valve is in a designated position for an amplification protocol.

FIG. 21 is a perspective view of the flow-control system 700 after the sample reservoirs 711-714 have been loaded with corresponding biological samples. In some embodiments, the rotary valve 704 includes gas reservoirs 741-744, which are shown in FIG. 20. During an amplification protocol, the gas reservoirs 741-744 are configured to align with the sample reservoirs 711-714. For example, as shown in FIG. 22, the sample reservoir 711 and the gas reservoir 741 combined to form a sample-preparation chamber 751. Gas within the gas reservoir 741 may function as a gas ballast in the sample-preparation chamber 751. After thermocycling, the biological samples may flow through the feed channel 756 (FIG. 20) that is in flow communication with the outlet port 736. As described herein, the biological samples may be directed to a reaction chamber, such as the reaction chamber 326 (FIG. 2), where designated reactions may occur and be detected.

Figure 23:
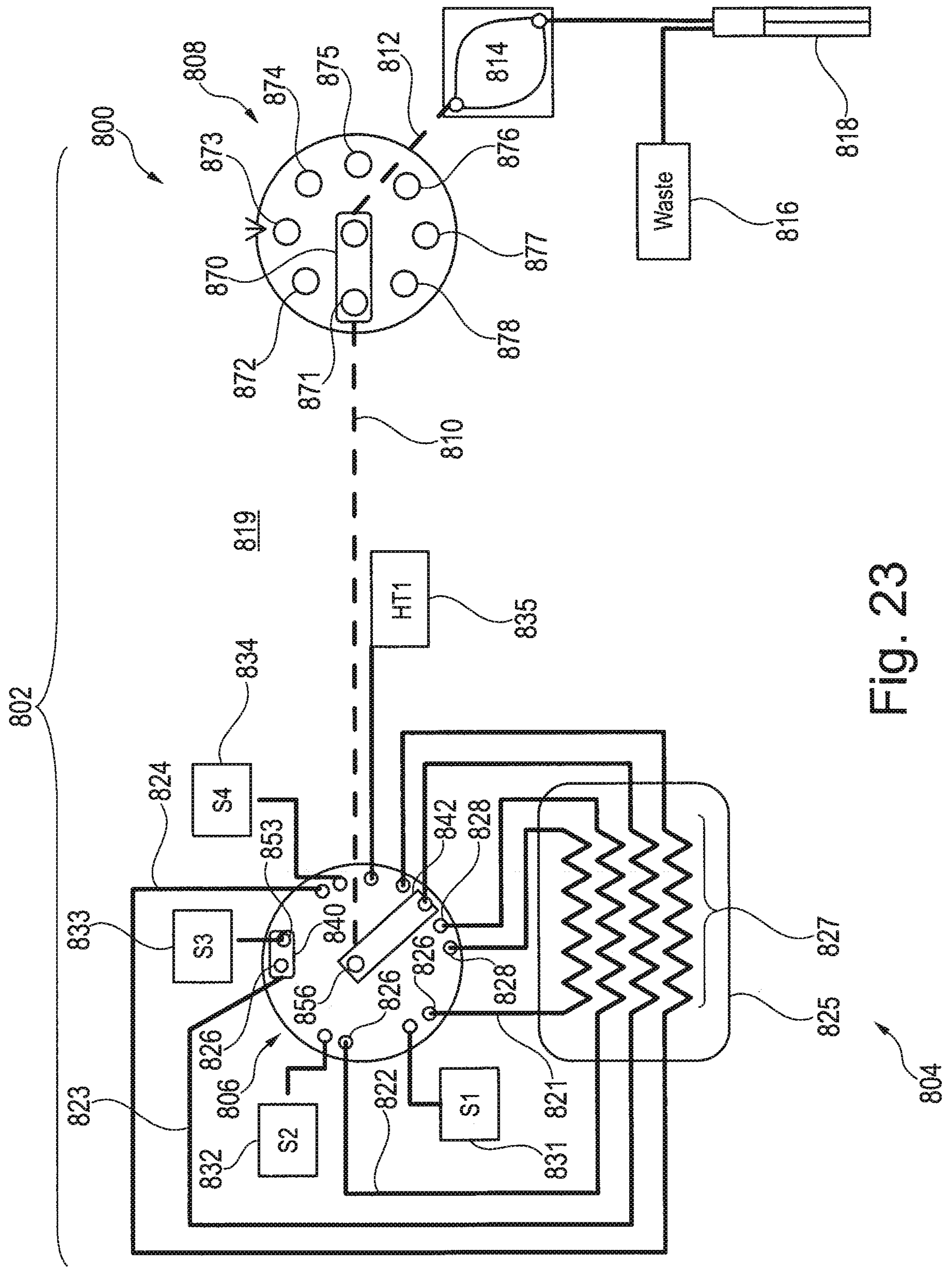
FIG. 23 is a schematic diagram of a system formed in accordance with an embodiment that is configured to conduct at least one of biochemical analysis or sample preparation.

FIG. 23 is a schematic view of a system 800 formed in accordance with an embodiment. The system 800 may include similar features as the system 100 (FIG. 1). For example, the system 800 includes a flow-control system 802 having a fluidic network 804. The fluidic network 804 may include a number of interconnected channels, ports, reservoirs, and other spatial regions that are configured to hold or have fluid flow therethrough. For example, the fluidic network 804 includes rotary valves 806, 808. The rotary valve 806 is configured to be used during a sample-preparation stage, and the rotary valve 808 is configured to be used during a sample-analysis stage. The rotary valves 806, 808 are fluidically coupled by an intermediate channel 810 of the fluidic network 804. The fluidic network 804 also includes a feed channel 812, a reaction chamber 814, and a waste reservoir 816. The flow-control system 802 includes a pump assembly 818 that is in flow communication with the fluidic network 804. In the illustrated embodiment, the pump assembly 818 includes a single pump, but may include multiple pumps in other embodiments. The system 800 may include a microfluidic body (not indicated) having a body side 819. The rotary valves 806, 808 are rotatably mounted to the body side 819. The microfluidic body may also include or define the intermediate channel 810 and the feed channel 812.

The fluidic network 804 also includes a plurality of assay channels 821-824 and a plurality of sample reservoirs 831-834. Each of the assay channels 821-824 extends between corresponding first and second ports 826, 828 and is configured to fluidically couple a corresponding sample reservoir to the intermediate channel 810. As shown, the assay channels 821-824 extend through a thermal-control area 825. In the illustrated embodiment, the assay channels 821-824 have wavy paths through the thermal-control area 825. The portions of the assay channels 821-824 that extend through the thermal-control area 825 may constitute sample-preparation regions 827. Alternatively or in addition to the non-linear paths, the assay channels 821-824 may have different dimensions to hold a designated volume of the corresponding biological samples.

The rotary valve 806 is configured to move between multiple valve positions. The rotary valve 806 includes a bridge channel 840 and a flow channel 842. The bridge channel 840 and the flow channel 842 are configured to fluidically couple one of the sample reservoirs 831-834 to the intermediate channel 810. For example, as shown in FIG. 23, the bridge channel 840 fluidically couples a reservoir port (or supply port) 853 of the sample reservoir 833 to the first port 826 of the assay channel 823. Simultaneously, the flow channel 842 fluidically couples the second port 828 to an intermediate port 856. The intermediate port 856 opens along the body side 819 and is in flow communication with the intermediate channel 810.

Accordingly, a system controller (not shown) may selectively rotate the rotary valve 806 to fluidically couple the sample reservoirs 831-834 to the corresponding assay channels 821-824, respectively. The system controller may selectively control the pump assembly 818 to induce flow of the biological samples within the sample reservoirs such that the biological samples are disposed within the sample-preparation regions 827 of the assay channels 821-824.

When the biological sample (or samples) is located within the corresponding assay channel, the rotary valve 806 may be rotated by the system controller to another valve position in which the first and second ports 826, 828 for each of the assay channels 821-824 are covered or sealed by the body side 819. With the assay channel(s) sealed, the biological sample(s) may undergo an amplification protocol. For instance, a thermocycler (not shown) may be positioned adjacent to the thermal-control area 825 and apply thermal energy in accordance with an amplification protocol. In particular embodiments, each of the biological samples may be positioned within the thermal-control area 825 at the same time. In alternative embodiments, the biological samples may be positioned within the thermal-control area 825 at separate times.

After the biological samples have been amplified, the rotary valve 806 may be returned to the corresponding valve positions to load the corresponding biological sample into the flow channel 842. With the biological sample disposed within the flow channel 842, the rotary valve may be rotated to another position in which the flow channel 842 is in flow communication with a reservoir 835. The reservoir 835 may contain, for example, a hydrogenation buffer solution. The biological sample may be loaded into the reservoir 835. Optionally, the rotary valve 806 and the pump assembly 818 may be operated in a similar manner to load the biological samples from the other assay channels into the reservoir 835. The biological samples may then be directed toward another stage. For example, the biological samples may flow through the flow channel 842, through the intermediate port 856, and into the intermediate channel 810. In alternative embodiments, the biological samples may be directed toward the rotary valve 808 without first being loaded into the reservoir 835.

As shown in FIG. 23, the rotary valve 808 includes a flow channel 870 and a plurality of reagent reservoirs 871-878. After the biological samples have been prepared using the rotary valve 806, the biological samples may be transported into the reaction chamber 814. Optionally, prior to the biological samples being delivered to the reaction chamber 814, the rotary valve 808 may be rotated to fluidically couple one or more of the reagent reservoirs 871-878 to the reaction chamber 814. More specifically, the flow channel 870 may be rotated to a designated position to fluidically couple one of the reagent reservoirs 871-878 to the reaction chamber 814. As such, the rotary valve 808 may be used to prepare the reaction chamber 814 for receiving the biological samples. For example, the reagent reservoirs 871-878 may include clustering reagents, enzymes, and/or capture probes.

After the biological samples are delivered to the reaction chamber 814, the rotary valve 808 may be selectively rotated to different valve positions. For example, the rotary valve 808 may be rotated in accordance with a predetermined cycle to repeatedly deliver reaction components for conducting an SBS protocol. The cycle may be similar to the cycle shown in Table 1 above. Accordingly, the rotary valve 808 may be utilized to prepare the reaction chamber for receiving the biological sample and/or to conduct an assay protocol.

Figure 24:
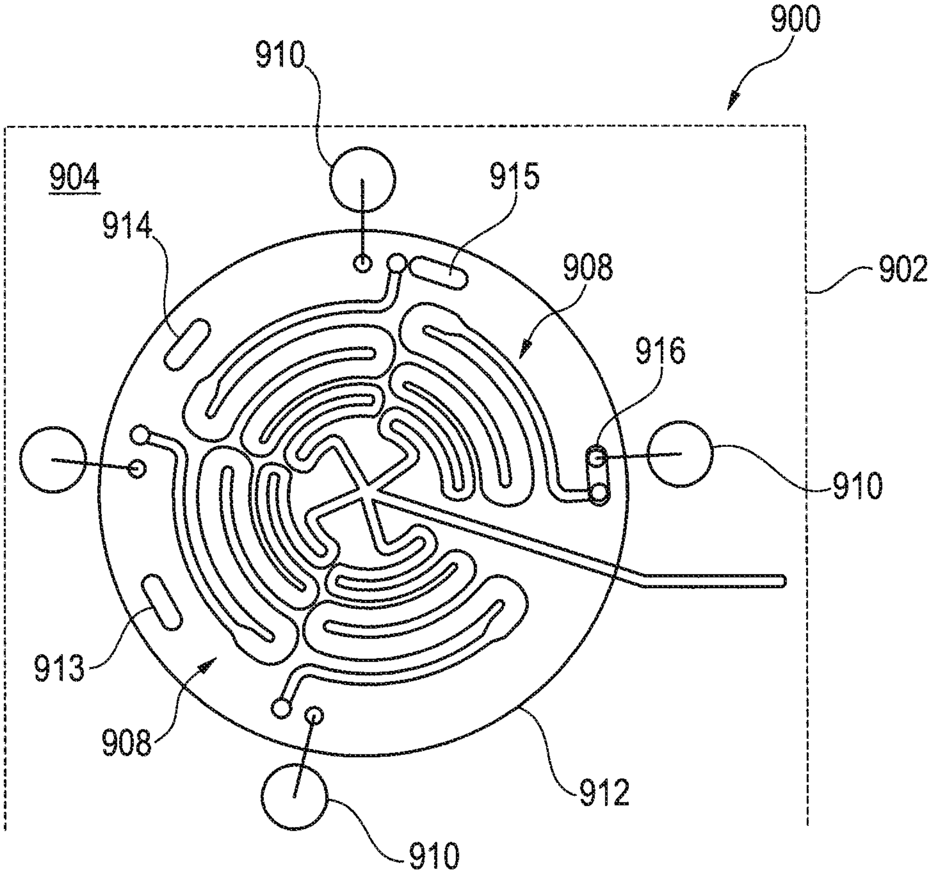
FIG. 24 is a plan view of a flow-control system formed in accordance with an embodiment that utilizes bridge channels.
Figure 25:
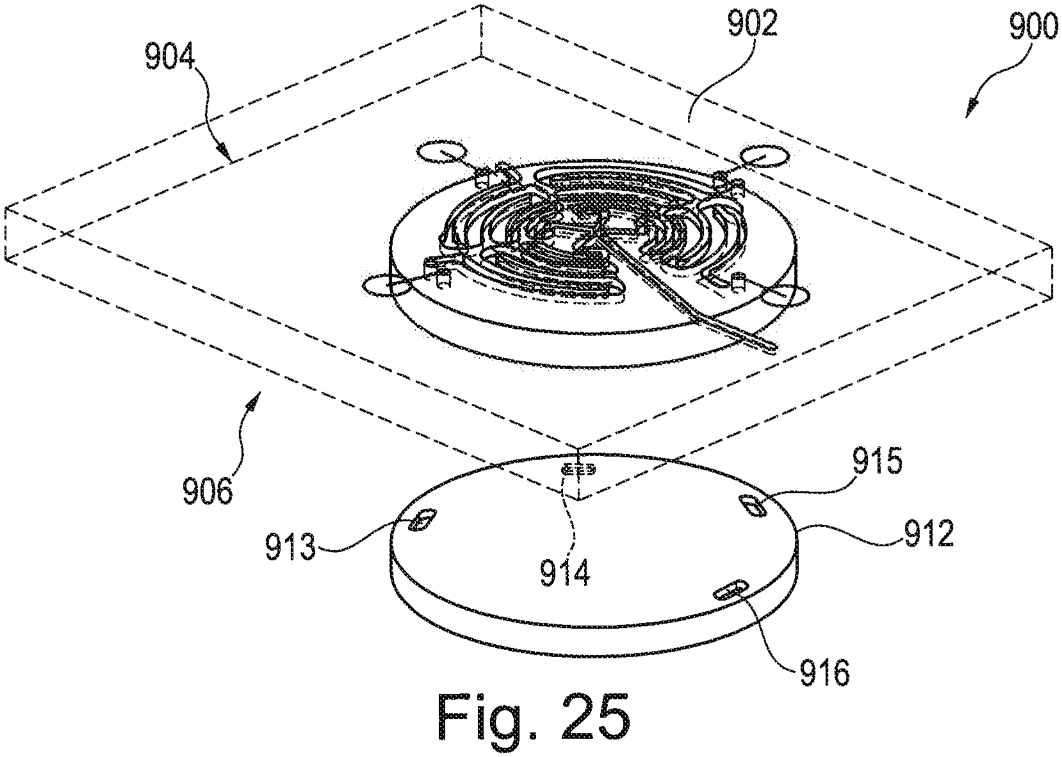
FIG. 25 is a partially exploded perspective view of the flow-control system of FIG. 24.

FIGS. 24 and 25 illustrate another embodiment that utilizes a rotary valve having a bridge channel. FIG. 24 is a plan view of a flow-control system 900, and FIG. 25 is a partially exploded perspective view of the flow-control system 900. As shown, the flow-control system 900 includes a microfluidic body 902 having opposite first and second body sides 904, 906 (FIG. 25). The microfluidic body 902 includes a plurality of flow channels 908 and a plurality of sample reservoirs 910. Each of the flow channels 908 is configured to be fluidically coupled to a respective sample reservoir 910. The flow channels 908 may be similar in shape and size to the flow channels 536-539 (FIG. 13).

The flow-control system 900 also includes a rotary valve 912. The rotary valve 912 includes a plurality of bridge channels 913-916 that are configured to fluidically couple the corresponding flow channels 908 and sample reservoirs 910. In particular embodiments, each of the bridge channels 913-916 is an open-sided groove along an exterior of the rotary valve 912. In alternative embodiments, the bridge channels 913-916 are not open-sided and, instead, extend between first and second ports that open to the exterior. By way of example, the bridge channel 916 in FIG. 24 fluidically couples a corresponding sample reservoir 910 to a corresponding flow channel 908 based on a rotational position of the rotary valve 912. As the biological sample flows through the bridge channel 913, the other bridge channels 914-916 are not fluidically coupled to the corresponding sample reservoir 910. More specifically, the other bridge channels 914-916 are sealed by the rotary valve 912.

In a similar manner as described in other embodiments, a thermocycler (not shown) may change a temperature that is experienced by the biological samples within the flow channels 908. For example, one or both of the body sides 904, 906 may be engaged by a thermocycler. After the amplification protocol, the biological samples may be delivered to another spatial region for additional modification/preparation and/or analysis.

As described above in the various embodiments, the rotary valve and the microfluidic body may include different fluidic elements that cooperate to control flow of one or more fluids in a designated manner. It is to be understood that the above embodiments are only illustrative, and not restrictive. For example, the above-described embodiments (and/or aspects thereof) may be used in combination with each other. In addition, many modifications may be made to adapt a particular situation or material to the teachings of the various embodiments without departing from its scope.

Figure 26:
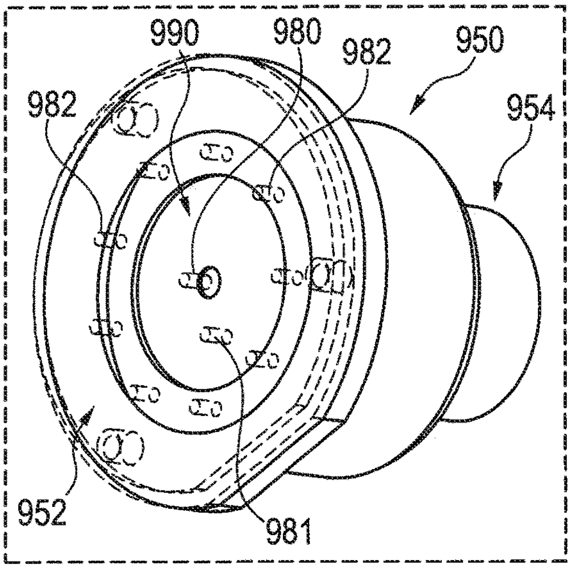
FIG. 26 is a bottom perspective view of a rotary valve in accordance with an embodiment.
Figure 27:
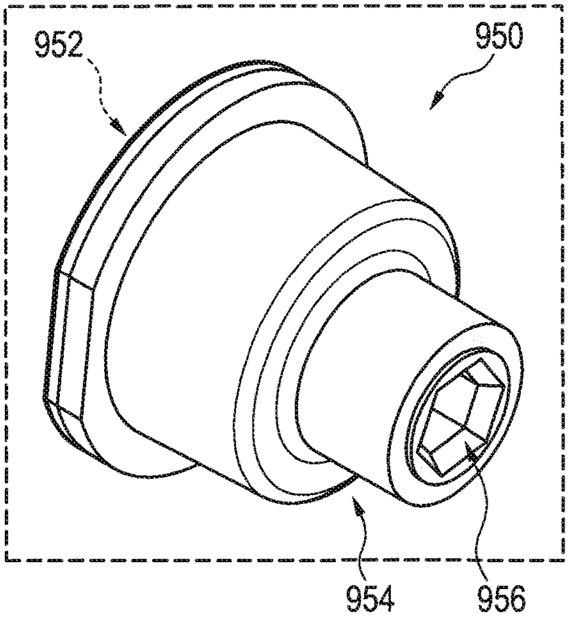
FIG. 27 is a side perspective view of the rotary valve of FIG. 26.

FIGS. 26-29 illustrate various views of a rotary valve 950 formed in accordance with an embodiment. The rotary valve 950 may be used as the rotary valve in various embodiments, such as the rotary valve 216 (FIG. 2). FIGS. 26 and 27 illustrate a bottom perspective view and a side perspective view, respectively, of the rotary valve 950. The rotary valve 950 includes a fluidic side 952 and an operative side 954. The operative side 954 includes a mechanical interface 956 that is configured to engage a valve actuator (not shown).

Figure 28:
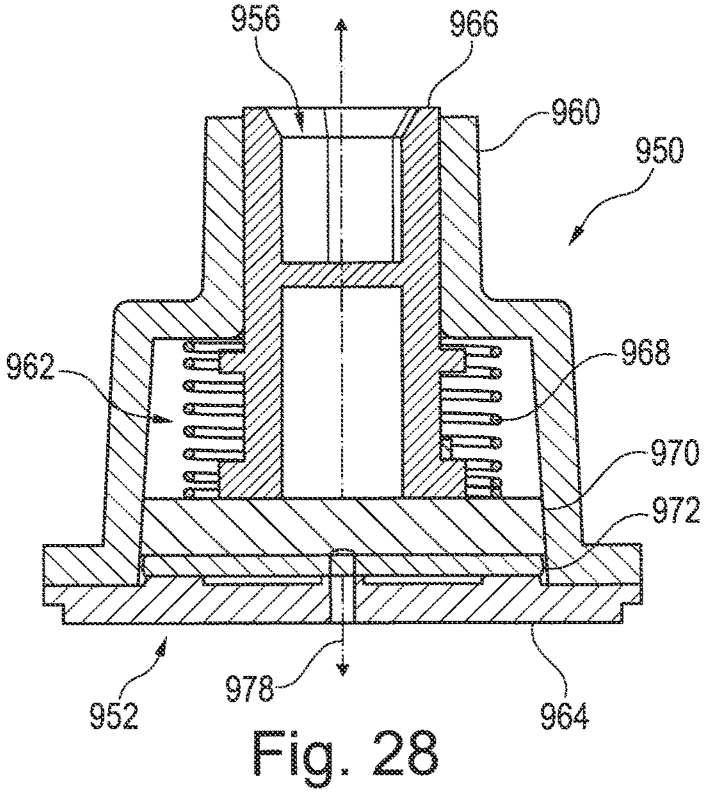
FIG. 28 illustrates a cross-section of the rotary valve of FIG. 26.

FIG. 28 illustrates a cross-section of the rotary valve 950. As shown, the rotary valve 950 includes a housing cover 960 and a side cover 964 that are secured in fixed positions with respect to each other. The housing cover 960 defines a valve cavity 962, and the side cover 964 closes one end of the valve cavity 962 along the fluidic side 952. The rotary valve 950 also includes a rotor shaft 966 that includes the mechanical interface 956, a valve spring 968, a manifold body 970, and a compressible membrane 972 that are each disposed within the valve cavity 962. The rotor shaft 966 is configured to rotate the manifold body 970 and the compressible membrane 972 alongside the side cover 964 about an axis 978.

The manifold body 970 is secured to the rotor shaft 966 on one side and secured to the compressible membrane 972 on an opposite side. The valve spring 968 may bias or urge the manifold body 970 and the compressible membrane 972 against an interior surface of the side cover 964. In particular embodiments, the compressible membrane 972 may be polypropylene or other similar material. Returning briefly to FIG. 26, the side cover 964 includes a central flow port 980, a drain port 981, and outer flow ports 982. The side cover 964 is partially transparent in FIG. 26 to indicate the central flow port 980, the drain port 981, and the outer flow ports 982. A total of nine outer flow ports 982 are shown, but other embodiments may include a different number of ports.

Figure 29:
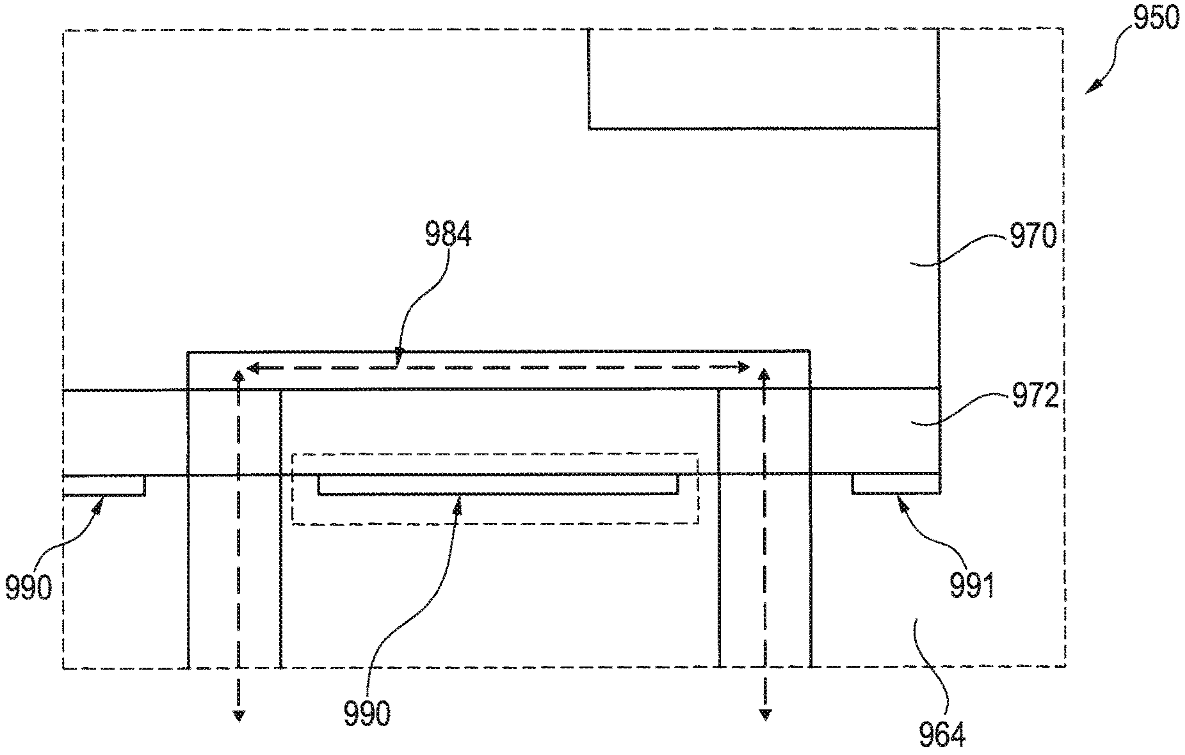
FIG. 29 is an enlarged cross-section of the rotary valve of FIG. 26.

FIG. 29 is an enlarged cross-section of the rotary valve 950 that indicates the interaction between the manifold body

970, the compressible membrane 972, and the side cover 964. As shown, the side cover 964 and the compressible membrane 972 may define a lubrication reservoir 990 therebetween. The lubrication reservoir 990 may extend around the axis 978. In some embodiments, an outer lubrication reservoir 991 may also be provided. The lubrication reservoirs 990 are also indicated in FIG. 26. The drain port 981 is in flow communication with the lubrication reservoir 990 so that a lubricant may be loaded into the reservoir 990. As shown, the manifold body 970 and the compressible membrane 972 define a flow channel 984 therebetween. When the rotor shaft 966 rotates the manifold body 970 with the compressible membrane 972, the flow channel 984 is rotated therewith. Frictional forces that resist rotation may be reduced because of the compressible membrane 972 and the lubrication reservoir 980. Accordingly, a lifetime operation of the rotary valve 950 may be longer than other known valves.

In accordance with an embodiment, a system is provided that includes a fluidic network having a sample channel, a reaction chamber, and a reservoir. The sample channel is in flow communication with a sample port that is configured to receive a biological sample. The system also includes a pump assembly that is configured to be in flow communication with the fluidic network. The system also includes a rotary valve that has a flow channel and is configured to rotate between first and second valve positions. The flow channel fluidically couples the reaction chamber and the sample channel when the rotary valve is in the first valve position and fluidically couples the reservoir and the reaction chamber when the rotary valve is in the second valve position. The pump assembly induces a flow of the biological sample toward the reaction chamber when the rotary valve is in the first valve position and induces a flow of a reaction component from the reservoir toward the reaction chamber when the rotary valve is in the second valve position.

In one aspect, the pump assembly may include a system pump that is in flow communication with the reaction chamber and is located downstream with respect to the reaction chamber.

In another aspect, the rotary valve may be configured to retain the biological sample in the flow channel as the rotary valve rotates from the first valve position to the second valve position. The pump assembly may be configured to induce a flow of the biological sample into the reservoir when the rotary valve is in the second valve position.

Optionally, the sample channel may be a first sample channel and the biological sample may be a first biological sample. The fluidic network may include a second sample channel having a second biological sample. The rotary valve may be configured to rotate to a third valve position such that the flow channel is in flow communication with the second sample channel. The pump assembly may be configured to induce a flow of the second biological sample in the second sample channel into the flow channel, wherein the rotary valve is configured to retain the second biological sample in the flow channel as the rotary valve rotates from the third valve position to the second valve position. The pump assembly may be configured to induce a flow of the second biological sample therein into the reservoir when the rotary valve is in the second valve position. In some embodiments, the pump assembly may be configured to induce a flow of the first and second biological samples from the reservoir toward the reaction chamber.

In another aspect, the reservoir may be a first reservoir. The fluidic network further may include a second reservoir, wherein the rotary valve may be configured to move to a third valve position such that the flow channel fluidically couples the second reservoir and the reaction chamber.

In another aspect, the sample channel may be a first sample channel and the fluidic network includes a second sample channel. Optionally, each of the first and second sample channels may be in flow communication with the rotary valve through a common supply port. Optionally, the system may also include a channel valve that is coupled to the sample channel. The channel valve may be configured to move between first and second positions to block flow and to permit flow, respectively, through the sample channel.

In another aspect, the rotary valve may rotate about an axis. The fluidic network may include a feed port that is aligned with the axis and fluidically couples the flow channel and the reaction chamber.

In another aspect, the fluidic network may also include a reagent channel. The sample channel and the reagent channel may be in flow communication with a common supply port that is located upstream with respect to the flow channel. The supply port may fluidically couple the sample channel and the reagent channel to the flow channel.

In another aspect, the system may include a detection assembly that is configured to detect designated reactions within the reaction chamber. Optionally, the detection assembly includes an imaging detector that may be positioned to detect light signals from the reaction chamber. Optionally, the imaging detector may have a fixed location with respect to the fluidic network.

In another aspect, the system includes a system controller that may be configured to automatically control the rotary valve and the pump assembly to conduct iterative cycles of a sequencing-by-synthesis (SBS) protocol.

In an embodiment, a method is provided that includes rotating a rotary valve having a flow channel to a first valve position. The flow channel is in flow communication with a reaction chamber when in the first valve position. The method may also include flowing a biological sample from a sample channel or a first reservoir through the flow channel and into the reaction chamber when the rotary valve is in the first valve position. The method may also include rotating the rotary valve to a second valve position. The flow channel may fluidically couple a second reservoir and the reaction chamber when in the second valve position. The method may also include flowing a reaction component from the second reservoir into the reaction chamber. The reaction component interacts with the biological sample within the reaction chamber.

In one aspect, the method may include detecting designated reactions between the reaction component and the biological sample within the reaction chamber. Optionally, detecting the designated reactions may include detecting light signals from the reaction chamber. The light signals may be indicative of the designated reactions.

In another aspect, the method also includes separately flowing a plurality of the biological samples into the reservoir thereby combining the biological samples therein. The biological samples may simultaneously flow through the flow channel and into the reaction chamber when the rotary valve is in the first valve position.

In another aspect, the method also includes rotating the rotary valve to a third valve position and flowing a wash solution from the third reservoir into the reaction chamber. The method may also include rotating the rotary valve to the second valve position and flowing the reaction component from the second reservoir into the reaction chamber. Optionally, the method includes executing iterative cycles of a sequencing-by-synthesis (SBS) protocol.

In another aspect, the method also includes amplifying the biological sample within the sample channel or the reservoir prior to flowing the biological sample through the flow channel and into the reaction chamber.

In an embodiment, a system is provided that includes a flow-control system having a fluidic network and a pump assembly that is in flow communication with the fluidic network. The fluidic network includes a sample channel that is configured to receive a biological sample, a plurality of reservoirs, and a reaction chamber. The system also includes a rotary valve having a flow channel. The rotary valve is configured to rotate to different valve positions to fluidically couple the reaction chamber to the sample channel or to one of the reservoirs. The system also includes a detection device that is configured to detect light signals from the reaction chamber during an assay protocol. The system also includes a system controller that is configured to control the rotary valve and the pump assembly to flow the biological sample from the sample channel and into the reaction chamber. The system controller is also configured to control the rotary valve, the pump assembly, and the detection device during a plurality of protocol cycles, wherein each of the protocol cycles includes: (a) rotating the rotary valve to a first reservoir-valve position such that the reaction chamber is in flow communication with a first reservoir of the plurality of reservoirs; (b) controlling the pump assembly to induce a flow of a fluid from the first reservoir into the reaction chamber; (c) rotating the rotary valve to a second reservoir-valve position such that the reaction chamber is in flow communication with a second reservoir of the plurality of reservoirs; (d) controlling the pump assembly to induce a flow of a fluid from the second reservoir into the reaction chamber; and (e) controlling the detection device to detect the light signals from the reaction chamber while the fluid from the second reservoir flows through the reaction chamber or after the fluid from the second reservoir flows through the reaction chamber.

In one aspect, the sample channel may include a sample-preparation region. The system may also include a thermocycler that is configured to control a temperature of the biological sample within the sample-preparation region. The system controller may control the thermocycler to amplify the biological sample within the sample-preparation region prior to flowing the biological sample from the sample channel into the reaction chamber.

Optionally, each of the protocol cycles includes rotating the rotary valve to a third reservoir-valve position such that the reaction chamber is in flow communication with a third reservoir of the plurality of reservoirs and controlling the pump assembly to induce a flow of a fluid from the third reservoir into the reaction chamber.

In another aspect, the detection device includes a CMOS imaging detector. In another aspect, a flow cell is coupled to the detection device. The flow cell may define the reaction chamber. Optionally, the flow cell is secured in a fixed position with respect to the detection device.

In another aspect, the flow-control system includes a microfluidic body having a body side. The body side may include a plurality of ports that open to the body side, wherein the rotary valve seals a plurality of the ports when the flow channel is fluidically coupled to at least one of the other ports. In particular embodiments, the system is configured to execute a sequencing-by-synthesis (SBS) protocol.

In accordance with an embodiment, a method is provided that includes providing a microfluidic body and a rotary valve. The microfluidic body has a body side and a fluidic network that includes a supply port and a feed port. The supply port opens to the body side. The rotary valve is rotatably mounted to the body side. The rotary valve has a first channel port, a second channel port, and a flow channel that extends between the first channel port and the second channel port. The method also includes rotating the rotary valve to a first valve position at which the first channel port is in flow communication with the supply port of the microfluidic body. The method also includes flowing a biological sample through the first channel port and into the flow channel when the rotary valve is in the first valve position. The method also includes rotating the rotary valve to a second valve position with the biological sample within the flow channel such that the first channel port is sealed by the body side. The method also includes performing a thermocycling operation to change a temperature of the biological sample in the flow channel to a select temperature.

In one aspect, the microfluidic body may include a reservoir port that opens to the body side and is in flow communication with a reservoir The method may also include rotating the rotary valve to align the first channel port and the reservoir port and inducing a flow of the biological sample within the flow channel through the first channel port into the reservoir. Optionally, the method includes inducing a flow of the biological sample from the reservoir through the flow channel and through the feed port of the microfluidic body.

In another aspect, the second channel port may be aligned with the feed port when the rotary valve is in the second valve position.

In another aspect, the second channel port may be sealed by the body side when the rotary valve is in the second valve position.

In another aspect, the first channel port is a first inlet port and the flow channel is a first flow channel. The rotary valve may include a second inlet port and a second flow channel. The second flow channel may extend between the second inlet port and the second channel port.

In another aspect, the first channel port is a first inlet port and the second channel port is a first outlet port. The rotary valve may include a second inlet port and a second outlet port with a flow channel extending therebetween.

In another aspect, the rotary valve may include a fluidic side and an operative side that face in opposite directions. The thermocycler may engage the operative side to control the temperature of the biological sample.

In another aspect, the method may include inducing a flow of the biological sample from the reservoir through the flow channel and through the feed port of the microfluidic body into a reaction chamber. The method may also include detecting light signals from the reaction chamber. Optionally, the reaction chamber has a remote location with respect to the rotary valve.

In another aspect, a flow cell includes the reaction chamber. Detecting the light signals from the reaction chamber may include detecting the light signals using an imaging detector that is coupled to the flow cell. Optionally, the imaging detector and the flow cell are secured to each other.

In accordance with an embodiment, a system is provided that includes a microfluidic body having a body side and a fluidic network that includes a supply port and a feed port. The supply port opens to the body side. The system also includes a rotary valve that is rotatably mounted to the body side. The rotary valve has a first channel port, a second channel port, and a flow channel that extends between the first and second channel ports. The rotary valve is configured to rotate between first and second valve positions. The first channel port is in flow communication with the supply port of the microfluidic body when the rotary valve is in the first valve position. The first channel port is sealed by the microfluidic body when the rotary valve is in the second valve position. The system also includes a pump assembly that is configured to induce a flow of a fluid through the supply port and into the flow channel when the rotary valve is in the first valve position. The system also includes a thermocycler that is positioned relative to the rotary valve and configured to control a temperature experienced by the fluid within the flow channel when the rotary valve is in the second valve position.

In one aspect, the microfluidic body may include a reservoir port that opens to the body side and is in flow communication with a reservoir. The rotary valve may be rotatable to a third valve position in which the first channel port and the reservoir port are aligned. The pump assembly may be configured to induce a flow of the fluid in the flow channel through the reservoir port and into the reservoir. Optionally, the pump assembly is configured to induce a flow of the fluid from the reservoir through the flow channel and through the feed port of the microfluidic body.

In another aspect, the rotary valve is configured to rotate about an axis. The second channel port and the feed port may be aligned with the axis.

In another aspect, the flow channel may be a first flow channel. The rotary valve may include a second flow channel that extends between corresponding channel ports.

In another aspect, the system includes a reaction chamber in flow communication with the feed port and a detection device that is positioned to detect designated reactions within the reaction chamber. Optionally, the reaction chamber has a remote location with respect to the rotary valve. Optionally, the system includes a flow cell having the reaction chamber. The detection device may be an imaging detector that is positioned adjacent to the flow cell. In some embodiments, the imaging detector and the flow cell may be secured to each other.

In accordance with an embodiment, a system is provided that includes a microfluidic body having a fluidic network that has an inlet port, an outlet port, and a sample reservoir. The system also includes a rotary valve that is rotatably coupled to the microfluidic body. The rotary valve has a first channel segment and a second channel segment. The first channel segment fluidically couples the inlet port and the sample reservoir when the rotary valve is in a first valve position. The second channel segment fluidically couples the outlet port and the sample reservoir when the rotary valve is in the first valve position. The system also includes a pump assembly configured to flow a fluid through the inlet port and the first channel segment into the sample reservoir when the rotary valve is in the first valve position. The rotary valve is configured to move to a second valve position in which the sample reservoir is sealed by the rotary valve. The system may also include a thermocycler that is positioned relative to the microfluidic body to provide thermal energy to the sample reservoir when the rotary valve is in the second valve position.

In one aspect, the rotary valve may include an enclosed gas reservoir. The enclosed gas reservoir may be aligned with the sample reservoir when the rotary valve is in the second valve position. The enclosed gas reservoir and the sample reservoir may combine to form a reaction chamber.

In another aspect, the system also includes a feed channel that is in flow communication with the outlet port. The feed channel may fluidically couple the outlet port to a reaction chamber. The system includes the reaction chamber and a detection device that is positioned to detect designated reactions within the reaction chamber.

In another aspect, the reaction chamber may have a remote location with respect to the rotary valve. Optionally, the system may include a flow cell having the reaction chamber. The detection device may be an imaging detector that is positioned adjacent to the flow cell.

In accordance with an embodiment, a system is provided that includes a microfluidic body having a fluidic network that has a sample reservoir and a separate assay channel. The assay channel extends between first and second ports. The fluidic network also includes a feed port. The system may also include a thermocycler that is positioned adjacent to a thermal-control area of the microfluidic body. The assay channel extends through the thermal-control area. The thermocycler is configured to provide thermal energy to the thermal-control area. The system also includes a rotary valve that is rotatably coupled to the microfluidic body and configured to move between first and second valve positions. The rotary valve has a bridge channel and a separate flow channel. The bridge channel fluidically couples the sample reservoir and the first port of the assay channel and the flow channel fluidically couples the second port of the assay channel and the feed port when the rotary valve is in the first valve position. The rotary valve is configured to move to a second valve position to seal the first and second ports of the assay channel.

In one aspect, the flow channel may be configured to receive a biological sample from the assay channel. The rotary valve may be configured to rotate to a third valve position in which the flow channel is fluidically coupled to a reservoir. The biological sample may be permitted to flow through the flow channel into the reservoir.

In another aspect, the system includes a reaction chamber that is in flow communication with the feed port and a detection device that is positioned to detect designated reactions within the reaction chamber. Optionally, the reaction chamber may have a remote location with respect to the rotary valve. Optionally, the system also includes a flow cell having the reaction chamber. The detection device may be an imaging detector that is positioned adjacent to the flow cell.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements whether or not they have that property.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a given module or unit may be added, or a given module or unit may be omitted.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The patentable scope should, therefore, be determined with reference to the appended claims, along with the full scope of equivalents to which such claims are entitled.

As used in the description, the phrase “in an exemplary embodiment” and the like means that the described embodiment is just one example. The phrase is not intended to limit the inventive subject matter to that embodiment. Other embodiments of the inventive subject matter may not include the recited feature or structure. In the appended claims, the terms “including” and “in which” are used as the plain-English equivalents of the respective terms “comprising” and “wherein.” Moreover, in the following claims, the terms “first,” “second,” and “third,” etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase “means for” followed by a statement of function void of further structure.

What is claimed is:

1. A system comprising:

a fluidic network comprising a sample channel, a reaction chamber, and a reservoir, the sample channel being in flow communication with a sample port that is configured to receive a biological sample, the reaction chamber having at least one optically transparent surface and a detector surface, the detector surface spaced apart from the at least one optically transparent surface, the detector surface having a plurality of reaction sites;

a pump assembly in flow communication with the fluidic network;

at least one light sensor configured to detect light signals generated by a reaction of at least one of the plurality of reaction sites within the reaction chamber;

a rotary valve comprising a flow channel, a bridge channel, and a feed port, the feed port fluidically coupled to the reaction chamber, the rotary valve rotatable between a first valve position, a second valve position, and a third valve position, the flow channel fluidically coupling the feed port of the rotary valve to the sample channel when the rotary valve is in the first valve position, the flow channel fluidically coupling the feed port to the reservoir when the rotary valve is in the second valve position, and the bridge channel fluidically coupling the reservoir with a first port when the rotary valve is in the third valve position, wherein the pump assembly is configured to induce a flow of the biological sample toward the reaction chamber when the rotary valve is in the first valve position, wherein the pump assembly is further configured to induce a flow of a reaction component from the reservoir toward the reaction chamber when the rotary valve is in the second valve position, and wherein the pump assembly is further configured to induce a flow of the reaction component from the reservoir toward the first port when the rotary valve is in the third position, wherein the rotary valve rotates about an axis, the feed port is aligned with the axis and fluidically couples the flow channel and the reaction chamber.

2. The system of claim 1, wherein the pump assembly comprises a single pump that is in flow communication with the reaction chamber and is located downstream with respect to the reaction chamber.

3. The system of claim 1, wherein the rotary valve retains the biological sample in the flow channel as the rotary valve rotates from the first valve position to a fourth valve position, the pump assembly inducing a flow of the biological sample into a buffer reservoir when the rotary valve is in the-fourth valve position.

4. The system of claim 3, wherein the sample channel is a first sample channel and the biological sample is a first biological sample, the fluidic network including a second sample channel having a second biological sample, the rotary valve rotatable to a fifth valve position such that the flow channel is in flow communication with the second sample channel, the pump assembly further configured to induce a flow of the second biological sample in the second sample channel into the flow channel, wherein the rotary valve retains the second biological sample in the flow channel as the rotary valve rotates from the fifth valve position to the fourth valve position, the pump assembly inducing a flow of the second biological sample therein into the reservoir when the rotary valve is in the fourth valve position.

5. The system of claim 1, wherein the reservoir is a first reservoir, the fluidic network further comprising a second reservoir, wherein the rotary valve moves to a fourth valve position such that the flow channel fluidically couples the second reservoir and the reaction chamber.

6. The system of claim 1, wherein the sample channel is a first sample channel and the fluidic network comprises a second sample channel.

7. The system of claim 6, wherein each of the first and second sample channels is in flow communication with the rotary valve through a common supply port.

8. The system of claim 6, further comprising a channel valve coupled to the sample channel, the channel valve movable between first and second positions to block flow and to permit flow, respectively, through the sample channel.

9. The system of claim 1, wherein the at least one light sensor is positioned adjacent to the detector surface of the reaction chamber and comprises an imaging detector configured to detect light signals from the reactions within the reaction chamber.

10. The system of claim 1, further comprising a system controller that automatically controls the rotary valve and the pump assembly to conduct iterative cycles of a sequencing-by-synthesis (SBS) protocol.

11. The system of claim 1, wherein the reaction is one of an associative binding event, dissociative binding event, release of a fluorescently labeled biomolecule from an analyte-of-interest, chemical transformation, chemical change, chemical interaction, fluorescence, luminescence, bioluminescence, chemiluminescence, biological reactions, nucleic acid replication, nucleic acid amplification, nucleic acid hybridization, nucleic acid ligation, phosphorylation, enzymatic catalysis, receptor binding, ligand binding, change in ion concentration, chemical binding interaction, or the addition or elimination of a proton.

* * * * *

UNITED STATES PATENT AND TRADEMARK OFFICE

CERTIFICATE OF CORRECTION

PATENT NO. : 10,596,569 B2
APPLICATION NO. : 15/315638
DATED : March 24, 2020
INVENTOR(S) : Sebastian Bohm et al.

It is certified that error appears in the above-identified patent and that said Letters Patent is hereby corrected as shown below:

In the Claims

In Column 44, Line 17, in Claim 3, delete “the-fourth” and insert -- the fourth --, therefor.

Signed and Sealed this
Thirtieth Day of June, 2020

Andrei Iancu
*Director of the United States Patent and Trademark Office*